United States Patent
Breschi et al.

(10) Patent No.: US 11,385,237 B2
(45) Date of Patent: Jul. 12, 2022

(54) METHODS FOR EVALUATING GLYCEMIC REGULATION AND APPLICATIONS THEREOF

(71) Applicant: The Board of Trustees of the Leland Stanford Junior University, Stanford, CA (US)

(72) Inventors: Alessandra Breschi, Stanford, CA (US); Michael P. Snyder, Stanford, CA (US); Dalia Perelman, Stanford, CA (US); Heather Hall, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 619 days.

(21) Appl. No.: 16/432,812

(22) Filed: Jun. 5, 2019

(65) Prior Publication Data
US 2019/0369108 A1   Dec. 5, 2019

Related U.S. Application Data

(60) Provisional application No. 62/681,014, filed on Jun. 5, 2018.

(51) Int. Cl.
| | | |
|---|---|---|
| *A61B 5/00* | (2006.01) | |
| *G01N 33/66* | (2006.01) | |
| *G16H 10/40* | (2018.01) | |
| *G16H 20/60* | (2018.01) | |
| *G16H 20/10* | (2018.01) | |
| *G16H 20/30* | (2018.01) | |
| *G16H 50/30* | (2018.01) | |
| *G16H 80/00* | (2018.01) | |
| *G16H 50/70* | (2018.01) | |
| *G01N 33/74* | (2006.01) | |

(52) U.S. Cl.
CPC ............. *G01N 33/66* (2013.01); *G16H 10/40* (2018.01); *G16H 20/10* (2018.01); *G16H 20/30* (2018.01); *G16H 20/60* (2018.01); *G16H 50/30* (2018.01); *G16H 50/70* (2018.01); *G16H 80/00* (2018.01); *G01N 33/74* (2013.01); *G01N 2800/042* (2013.01)

(58) Field of Classification Search
CPC .. G01N 33/66; G01N 33/74; G01N 2800/042; G16H 20/30; G16H 10/40; G16H 50/30; G16H 50/70; G16H 20/10; G16H 20/60; G16H 80/00
See application file for complete search history.

(56) References Cited

U.S. PATENT DOCUMENTS

2014/0031658 A1* 1/2014 Zheng ................ A61B 5/14532
                                                      600/365
2020/0342974 A1* 10/2020 Chen ...................... G16H 20/17

OTHER PUBLICATIONS

"Standards of Medical Care in Diabetes—2017", American Diabetes Association, The Journal of Clinical and Applied Research and Education, vol. 40, Supp. 1, Jan. 2017, 142 pgs.

(Continued)

*Primary Examiner* — Mohamed Charioui
*Assistant Examiner* — Christine Y Liao
(74) *Attorney, Agent, or Firm* — KPPB LLP

(57) ABSTRACT

Classification of individuals based on their glycemic pattern and applications thereof are described. Generally, systems utilize continuous glucose monitoring data to determine glycemic pattern variability, which can be used as a basis to classify and treat individuals.

16 Claims, 21 Drawing Sheets

(56) References Cited

OTHER PUBLICATIONS

Ahlqvist et al., "Novel subgroups of adult-onset diabetes and their association with outcomes: a data-driven cluster analysis of six variables", The Lancet Diabetes & Endocrinology, vol. 6, No. 5, May 1, 2018, pp. 361-369.
Albert et al., "Smart Meter Driven Segmentation: What Your Consumption Says About You", IEEE Transactions on Power Systems, vol. 28, No. 4, Nov. 2013, 12 pgs.
Baghurst, "Calculating the Mean Amplitude of Glycemic Excursion from Continuous Glucose Monitoring Data: An Automated Algorithm", Diabetes Technology & Therapeutics, vol. 13, No. 3, Feb. 27, 2011, pp. 296-302.
Batista et al., "A Complexity-Invariant Distance Measure for Time Series", Proceedings of the 2011 SIAM International Conference on Data Mining, Mesa, Arizona, Apr. 28-30, 2011, 12 pgs.
Bersch et al., "Sensor Data Acquisition and Processing Parameters for Human Activity Classification", Sensors, vol. 14, No. 3, Mar. 4, 2014, pp. 4239-4270.
Crenier et al., "Glucose Variability Assessed by Low Blood Glucose Index Is Predictive of Hypoglycemic Events in Patients With Type 1 Diabetes Switched to Pump Therapy", Diabetes Care, vol. 36, No. 8, Aug. 2013, pp. 2148-2153.
DPPR Group, "Reduction in the Incidence of Type 2 Diabetes with Lifestyle Intervention or Metformin", The New England Journal of Medicine, vol. 346, No. 6, Feb. 7, 2002, pp. 393-403.
Garber, "Postprandial Dysmetabolism and the Heart", Heart Failure Clinics, vol. 8, No. 4, Oct. 2012, pp. 563-573.
Giorgino, "Computing and Visualizing Dynamic Time Warping Alignments in R: The dtw Package", Journal of Statistical Software, vol. 31, No. 7, Aug. 2009, 24 pgs.
Halkidi et al., "On Clustering Validation Techniques", Journal of Intelligent Information Systems, vol. 17, No. 2/3, 2001, pp. 107-145.
Herman et al., "The Cost-Effectiveness of Lifestyle Modification or Metformin in Preventing Type 2 Diabetes in Adults with Impaired Glucose Tolerance", Annals Internal Medicine, vol. 142, No. 5, Mar. 1, 2005, pp. 323-332.
Holst et al., "Loss of Incretin Effect Is a Specific, Important, and Early Characteristic of Type 2 Diabetes", Diabetes Care, vol. 34, No. 2, May 2011, pp. S251-S257.
Hovorka et al., "ISEC: a program to calculate insulin secretion", Computer Methods and Programs in Biomedicine, vol. 50, No. 3, Aug. 1996, pp. 253-264.
Jung, "Clinical Implications of Glucose Variability: Chronic Complications of Diabetes", Endocrinology and Metabolism, vol. 30, No. 2, Jun. 30, 2015, pp. 167-174.
Li et al., "The long-term effect of lifestyle interventions to prevent diabetes in the China Da Qing Diabetes Prevention Study: a 20-year follow-up study", The Lancet, vol. 371, No. 9626, May 24, 2008, pp. 1783-1789.
Luxburg, "A tutorial on spectral clustering", Statistics and Computing, vol. 17, No. 4, Dec. 2007, pp. 395-416.
Meyer et al., "proxy: Distance and Similarity Measures", Package 'proxy', Version 0.4-20, Retrieved from: https://mran.microsoft.com/snapshot/2017-12-21/web/packages/proxy/proxy.pdf, Dec. 12, 2017, 10 pgs.
Monnier et al., "Activation of oxidative stress by acute glucose fluctuations compared with sustained chronic hyperglycemia in patients with type 2 diabetes", JAMA Network, vol. 295, No. 14, Apr. 12, 2006, pp. 1681-1687.
Monnier et al., "The Effect of Glucose Variability on the Risk of Microvascular Complications in Type 1 Diabetes", Diabetes Care, vol. 30, No. 1, Jan. 2007, pp. 187-188.
Nathan et al., "Impaired Fasting Glucose and Impaired Glucose Tolerance", Diabetes Care, vol. 30, No. 3, Mar. 2007, pp. 753-759.
Suh et al., "Glycemic Variability: How Do We Measure It and Why Is It Important?", Diabetes & Metabolism Journal, vol. 39, No. 4, Aug. 2015, pp. 273-282.
Tabak et al., "Prediabetes: A High-Risk State for Diabetes Development", The Lancet, vol. 379, No. 9833, Jun. 16, 2012, pp. 2279-2290.
Tuomilehto et al., "Prevention of Type 2 Diabetes Mellitus by Changes in Lifestyle among Subjects with Impaired Glucose Tolerance", The New England Journal of Medicine, vol. 344, No. 18, May 3, 2001, pp. 1343-1350.
Tuzcu et al., "Dynamic Time Warping As a Novel Tool in Pattern Recognition of ECG Changes in Heart Rhythm Disturbances", Proceedings of the IEEE International Conference on Systems, Man and Cybernetics, Waikoloa, Hawaii, Oct. 10-12, 2005, 5 pgs.
Van Cauter et al., "Estimation of Insulin Secretion Rates from C-Peptide Levels: Comparison of Individual and Standard Kinetic Parameters for C-Peptide Clearance", Diabetes, vol. 41, No. 3, Mar. 1992, pp. 368-377.
Wang et al., "Similarity network fusion for aggregating data types on a genomic scale", Nature Methods, vol. 11, No. 3, Mar. 2014, Online Publication: Jan. 26, 2014, pp. 333-337.
Wojcicki, ""J"-Index. A New Proposition of the Assessment of Current Glucose Control in Diabetic Patients", Hormone and Metabolic Research, vol. 27, No. 1, 1995, pp. 41-42.
Zeevi et al., "Personalized Nutrition by Prediction of Glycemic Responses", Cell, vol. 163, No. 5, Nov. 19, 2015, pp. 1079-1094.
Zhao et al., "GMD: Generalized Minimum Distance of distributions", Package 'GMD', Version 0.3.3, Retrieved from: https://mran.microsoft.com/snapshot/2016-10-12/web/packages/GMD/GMD.pdf, Feb. 19, 2015, 35 pgs.

* cited by examiner

Fig. 5
1) Patient enrollment and data collection
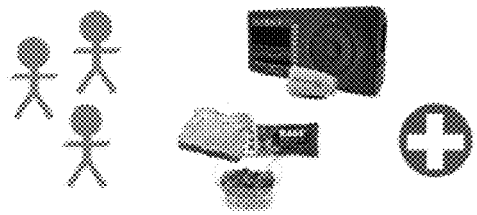
2) Identify patterns from CGM
3) Classify patterns with spectral clustering
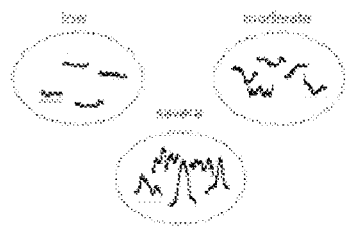
4) Compare with clinical features
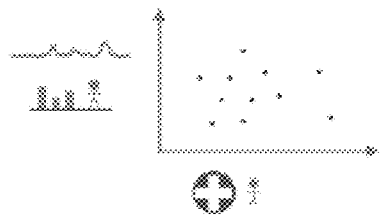
5) Determine effects of standardized meals
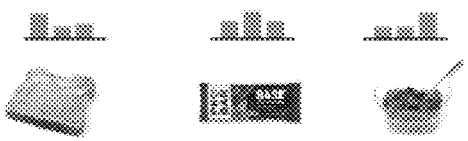
6) Early indication of diabetes and prediction of insulin resistance
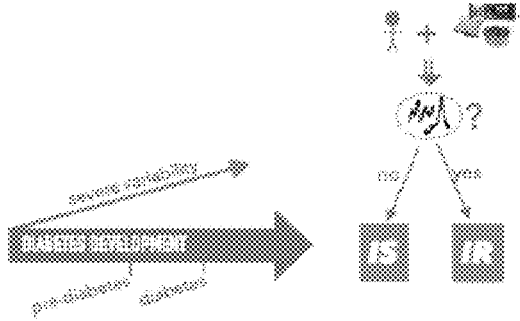

Fig. 6

| | userID | DaysCGM | Age | BMI | SSPG | insulin | FBG | OGTT | HbA1C | hsCRP | Tri/HDL | timedMeals |
|---|---|---|---|---|---|---|---|---|---|---|---|---|
| 1 | 1636-69-001 | 429 | 59 | 21.7 | 91 | 9 | 109 | 205 | 6.7 | 0.3 | 2 | |
| 2 | 1636-69-026 | 14 | 67 | 28.0 | 133 | 7 | 97 | 152 | 6.2 | 1.2 | 0.9 | |
| 3 | 1636-69-028 | 23 | 50 | 27.3 | 75 | 4 | 91 | 121 | 5.2 | 4.4 | 0.5 | |
| 4 | 1636-69-032 | 14 | 59 | 25 | 87 | 5 | 82 | 142 | 5.7 | 0.2 | 2.5 | |
| 5 | 1636-69-035 | 14 | 60 | 28.2 | 160 | | 87 | 118 | 5.5 | 0.2 | 1.5 | |
| 6 | 1636-69-048 | 14 | 60 | 33.5 | 119 | 6 | 87 | 130 | 5.2 | 4.8 | 3.5 | |
| 7 | 1636-69-053 | 28 | 60 | 26.2 | 188 | 5 | 85 | 128 | 5 | 0.4 | 1.5 | |
| 8 | 1636-69-060 | 14 | 55 | 28.3 | 179 | | 91 | 120 | 5.2 | 1.4 | 1.7 | |
| 9 | 1636-69-064 | 76 | 51 | 28.3 | 198 | 6 | 82 | 137 | 5.2 | 1.1 | 2.8 | |
| 10 | 1636-69-069 | 21 | 56 | 29.3 | 250 | 7 | 90 | 111 | 5.5 | 1.4 | 2.9 | |
| 11 | 1636-69-090 | 14 | 76 | 22 | | 14 | 106 | 194 | 5.6 | 0 | 0.4 | |
| 12 | 1636-69-093 | 14 | 62 | 23.8 | 155 | 18 | 127 | 151 | 6.5 | 1.1 | 10.4 | |
| 13 | 1636-69-100 | 27 | 45 | 28.4 | | 3 | 83 | 66 | 5.3 | 0.3 | 1.7 | |
| 14 | 1636-69-104 | 21 | 56 | 24.6 | 129 | 5 | 82 | 104 | 4.6 | 2.5 | 0.9 | |
| 15 | 1636-69-107 | 29 | 53 | 38 | 223 | 12 | 98 | 120 | 5.6 | 2.3 | 2.7 | |
| 16 | 1636-69-111 | 22 | 48 | 29.2 | | 11 | 95 | 97 | 5.2 | 0.5 | 1.1 | |
| 17 | 1636-69-114 | 28 | 65 | 29.5 | | 5 | 91 | 117 | 5.8 | 1.3 | 0.9 | |
| 18 | 1636-69-123 | 40 | 54 | 23.8 | | 8 | 86 | 116 | 5.3 | 0.7 | 0.4 | |
| 19 | 1636-69-69-093 | 14 | | | | | | | | | | |
| 20 | 1636-70-1002 | 7 | 51 | 28.8 | 175 | 20 | 88 | 98 | 5.2 | 4.4 | 3.4 | |
| 21 | 1636-70-1003 | 14 | 51 | 26.2 | 70 | 7 | 76 | 107 | 5.2 | 0.9 | 0.4 | |
| 22 | 1636-70-1005 | 39 | 66 | 27.2 | 99 | 5 | 94 | 152 | 5.5 | 0.4 | 1.5 | |
| 23 | 1636-70-1008 | 19 | 62 | 28 | 229 | 18 | 82 | 124 | 5.4 | 1.8 | 3.4 | |
| 24 | 1636-70-1010 | 27 | 68 | 33 | 65 | 9 | 94 | 190 | 5.5 | 3.5 | 1.3 | |
| 25 | 2133-001 | 14 | 27 | 26.4 | 110 | 7 | 86 | 101 | 5.2 | 1.1 | 2.5 | 6 |
| 26 | 2133-002 | 20 | 29 | 21.4 | 143 | 9 | 76 | 90 | 5.3 | 1.7 | 2.1 | 6 |
| 27 | 2133-003 | 12 | 36 | 24.6 | 110 | 13 | 91 | 131 | 5.4 | 0.4 | 3.9 | |
| 28 | 2133-004 | 21 | 54 | 28.1 | 173 | 11 | 145 | | 6 | 1.6 | 3.3 | 6 |
| 29 | 2133-006 | 14 | 29 | 20 | 61 | 6 | 80 | 67 | 5.3 | 0.2 | 0.4 | 6 |
| 30 | 2133-007 | 12 | 48 | 26.5 | 218 | 10 | 95 | 127 | 5.5 | 8.6 | 1.4 | |
| 31 | 2133-008 | 14 | 31 | 19 | | | | | | | | 5 |
| 32 | 2133-009 | 15 | 25 | 19.5 | | 5 | 84 | 113 | 5.2 | 3.3 | 1.8 | 6 |
| 33 | 2133-010 | 21 | 29 | 24.5 | | 8 | 91 | 125 | | 0.6 | 0.8 | 6 |
| 34 | 2133-011 | 22 | 32 | 24 | 69 | 5 | 88 | 114 | 5.4 | 0 | 0.4 | 6 |
| 35 | 2133-012 | 16 | 27 | 20 | | 4 | 83 | 113 | 5.3 | 2.1 | 0.3 | 6 |
| 36 | 2133-013 | 14 | 65 | 23.6 | | 7 | 89 | 85 | 5.4 | 0.3 | 1.2 | 5 |
| 37 | 2133-015 | 16 | 51 | 33.6 | 158 | 10 | 96 | 181 | 5.7 | 5.4 | 2.4 | 4 |
| 38 | 2133-017 | 18 | 47 | 40.4 | | 11 | 98 | 164 | 5.3 | 3.8 | 1.7 | 5 |
| 39 | 2133-018 | 15 | 64 | 26.4 | 185 | 7 | 103 | 256 | 6.4 | 0 | 1.1 | 6 |
| 40 | 2133-019 | 16 | 64 | 29.9 | | 6 | 85 | | 6.2 | 1.4 | 0.7 | 6 |
| 41 | 2133-020 | 15 | 53 | 24.8 | 57 | 2 | 82 | 97 | 5.1 | 0.2 | 0.8 | 6 |
| 42 | 2133-021 | 15 | 56 | 27.9 | 130 | 5 | 119 | 187 | 6 | 0.5 | 2.7 | 6 |
| 43 | 2133-022 | 23 | 60 | 28 | 111 | 6 | 85 | 116 | 4.9 | 0.7 | 0.6 | |
| 44 | 2133-023 | 21 | 52 | 25.9 | 70 | 6 | 91 | 65 | 5.2 | 3.1 | 2.3 | |
| 45 | 2133-024 | 27 | 38 | 24.5 | 40 | 20 | 124 | 95 | 5.2 | 0.2 | 5.4 | 6 |
| 46 | 2133-025 | 20 | 64 | 23.6 | | 2 | 91 | 139 | 5.1 | 1.4 | 0.4 | 6 |
| 47 | 2133-026 | 28 | 34 | 21.3 | 73 | 4 | 91 | 77 | 5.1 | 0 | 0.7 | 6 |
| 48 | 2133-027 | 23 | 58 | 28.3 | 55 | 8 | 107 | 102 | 5.5 | 11 | 2.7 | |
| 49 | 2133-028 | 32 | 25 | 24.0 | | 3 | 89 | 63 | 5 | 0.2 | 1 | |
| 50 | 2133-030 | 38 | 31 | 23 | 45 | 3 | 90 | 84 | 5.4 | 0.2 | 0.6 | 5 |
| 51 | 2133-032 | 29 | 35 | 26.3 | 59 | 3 | 93 | 134 | 5.1 | 0.3 | 0.6 | 6 |
| 52 | 2133-033 | 14 | 42 | 19.6 | 51 | | 90 | 100 | 5 | 0.2 | 0.6 | 6 |
| 53 | 2133-035 | 22 | 61 | 30.1 | | 8 | 105 | 108 | 5.4 | 1 | 1.4 | 6 |
| 54 | 2133-036 | 19 | 30 | 39.2 | 301 | 12 | 98 | 177 | 5.9 | 9 | 1.5 | 6 |
| 55 | 2133-037 | 24 | 28 | 25.4 | 64 | 5 | 83 | 107 | 4.9 | 3.8 | 1.1 | 6 |
| 56 | 2133-039 | 23 | 46 | 36.1 | 335 | 14 | 100 | 240 | 5.1 | 5.5 | 2.9 | 6 |
| 57 | 2133-040 | 19 | 39 | 21 | 148 | 4 | 86 | 105 | 5.2 | 1.2 | 1.4 | 6 |
| 58 | 2133-041 | 18 | 51 | 27.3 | 58 | 3 | 93 | 74 | 4.9 | 0.4 | 1.1 | 5 |

Table on Panel Characteristics

Fig. 7

| variable | all | non-diabetic | pre-diabetic | diabetic |
|---|---|---|---|---|
| Clinical and Laboratory Results | | | | |
| — age | 48.9 +/- 13.8 | 44.8 +/- 12.9 | 56.9 +/- 13.9 | 57 +/- 7.2 |
| — sex (F/M) | 32/25 | 23/15 | 8/6 | 1/4 |
| — BMI | 26.7 +/- 4.7 | 25.4 +/- 3.9 | 29.8 +/- 5.3 | 27.2 +/- 5.5 |
| — SSPG | 129.8 +/- 71.3 | 122.6 +/- 63.4 | 119.7 +/- 77.7 | 187.8 +/- 89.9 |
| — hemoglobin A1C | 5.4 +/- 0.4 | 5.2 +/- 0.2 | 5.7 +/- 0.3 | 6.1 +/- 0.6 |
| — fasting blood glucose | 93.2 +/- 12.6 | 87.3 +/- 5.1 | 100.4 +/- 11 | 116.8 +/- 18.9 |
| — 2hr OGTT | 124.8 +/- 41.5 | 106.1 +/- 21.6 | 150.8 +/- 35.4 | 213 +/- 46.5 |
| — fasting insulin | 7.8 +/- 4.4 | 6.7 +/- 4.2 | 8.9 +/- 4.3 | 11.8 +/- 4.3 |
| — high sensitivity CRP | 1.9 +/- 2.4 | 1.5 +/- 1.8 | 2.8 +/- 3.5 | 1.7 +/- 2.2 |
| — total cholesterol | 185.9 +/- 39.9 | 183.2 +/- 35.2 | 195.2 +/- 39.3 | 180.6 +/- 72.7 |
| — triglycerides | 96.2 +/- 63.7 | 81.5 +/- 51.5 | 113.9 +/- 62.3 | 154.8 +/- 109.5 |
| — HDL | 62.1 +/- 15.8 | 62 +/- 15.1 | 67.9 +/- 15.1 | 46 +/- 14.4 |
| — LDL | 104.8 +/- 37.9 | 104.8 +/- 35.5 | 105.1 +/- 39.9 | 103.4 +/- 56.3 |
| Sensor Glucose Metrics | | | | |
| — mean | 100.5 +/- 11.3 | 96.6 +/- 10.2 | 105.5 +/- 9 | 115.7 +/- 7.3 |
| — standard deviation | 20.2 +/- 5.2 | 18.4 +/- 3.7 | 22.1 +/- 3.7 | 28.8 +/- 8.1 |
| — range | 154.7 +/- 44.5 | 144.5 +/- 38 | 156.1 +/- 22.2 | 228.8 +/- 69.9 |
| — minimum | 47.1 +/- 7.4 | 45.8 +/- 6.5 | 49.1 +/- 7.8 | 51 +/- 10.8 |
| — max | 201.8 +/- 45 | 190.3 +/- 37.6 | 205.2 +/- 20.3 | 279.8 +/- 70.8 |
| — mean slope | 12 +/- 1.9 | 11.9 +/- 2 | 12 +/- 1.7 | 12.4 +/- 2.2 |
| — max slope | 225.4 +/- 122.8 | 220.8 +/- 96 | 212.1 +/- 136.6 | 297 +/- 240.4 |
| — number fluctuations >140mg/dL | 0.1 +/- 0.2 | 0 +/- 0.1 | 0.1 +/- 0.2 | 0.4 +/- 0.3 |
| Glucose Variability Metrics | | | | |
| — number fluctuations >200mg/dL | 0.1 +/- 0.2 | 0 +/- 0.1 | 0.1 +/- 0.2 | 0.4 +/- 0.3 |
| — number of excursions >SD | 3.8 +/- 1.2 | 4.2 +/- 1.3 | 3.4 +/- 0.7 | 2.8 +/- 0.8 |
| — MAGE | 35 +/- 14.6 | 31.7 +/- 11.2 | 36.4 +/- 11.8 | 56.4 +/- 26.1 |
| — j index | 0.1 +/- 0 | 0.1 +/- 0 | 0.1 +/- 0 | 0.1 +/- 0 |
| — interquantile range | 23.6 +/- 5.6 | 21.8 +/- 4.5 | 26.4 +/- 5.8 | 28.9 +/- 6.4 |
| — mean of daily differences | 13.6 +/- 4 | 12.4 +/- 3.5 | 15.2 +/- 3.6 | 18 +/- 4.9 |
| — mean daily distance traveled | 345.2 +/- 87.7 | 334 +/- 87.5 | 355.2 +/- 80.1 | 402.5 +/- 102 |
| — coefficient of variation | 0.2 +/- 0 | 0.2 +/- 0 | 0.2 +/- 0 | 0.2 +/- 0.1 |

Table on Panel Characteristics Separated into Cohorts as determined by the Standardized Diagnosis Protocol of American Association of Diabetes

Fig. 11

| variable | low | moderate | severe | p.value |
|---|---|---|---|---|
| coef_variation | 0.09 | 0.08 | 0.11 | 9.7e-159 |
| distance_traveled | 41.28 | 46.47 | 71.83 | <1e-100 |
| IQR_glucose | 8.82 | 10.48 | 21.14 | <1e-100 |
| j_index | 0.08 | 0.1 | 0.14 | <1e-100 |
| MAGE | 14.32 | 16.3 | 29.75 | <1e-100 |
| max_glucose | 90.41 | 110.47 | 145.49 | <1e-100 |
| max_slope | 38.57 | 41.03 | 55.37 | 2.4e-191 |
| mean_glucose | 77.48 | 96.27 | 122.26 | <1e-100 |
| mean_slope | 9.76 | 10.7 | 15.28 | <1e-100 |
| min_glucose | 67.34 | 84.28 | 100.96 | <1e-100 |
| sd_window | 6.61 | 7.62 | 13.91 | <1e-100 |

Table on Comparison of Common CGM Metrics Between Glucotypes

Fig. 13

| | hemoglobin A1c | fasting blood sugar | OGTT - 2hr | fasting insulin | SSPG | triglycerides/HDL |
|---|---|---|---|---|---|---|
| moderate | -0.163 | -0.198 | -0.161 | 0.179 | -0.015 | 0.156 |
| low | -0.386 ** | -0.285 * | -0.505 *** | -0.266 . | -0.416 ** | -0.226 . |
| severe | 0.442 ** | 0.378 ** | 0.553 *** | 0.107 | 0.322 * | 0.083 |
| IQR | 0.377 ** | 0.43 ** | 0.42 ** | 0.094 | 0.083 | 0.058 |
| j_index | 0.583 *** | 0.478 *** | 0.703 *** | 0.198 | 0.418 ** | 0.197 |
| coef_variation | 0.246 . | 0.277 * | 0.42 ** | 0.076 | 0.06 | -0.009 |
| mage | 0.398 * | 0.304 . | 0.736 *** | 0.205 | 0.32 . | 0.009 |
| sd_glucose | 0.462 *** | 0.418 ** | 0.648 *** | 0.144 | 0.261 . | 0.091 |
| mean_glucose | 0.576 *** | 0.454 *** | 0.649 *** | 0.203 | 0.438 ** | 0.225 . |

Table on Correlation of Common CGM Variability Metrics and Glucose Homeostasis significance codes: 0 = '*', 0.001 = '', 0.01 = '*', 0.05 = '.' .

Fig. 15

| Nutrients | Bread and peanut butter | Energy bar | Cereal milk and raisins |
|---|---|---|---|
| calories | 430 | 370 | 280 |
| fat (g) | 20 | 18 | 2.5 |
| carbohydrates (g) | 51 | 48 | 54 |
| -sugar (g) | 12 | 19 | 35.2 |
| -fiber (g) | 12 | 6 | 3.3 |
| protein (g) | 18 | 9 | 11 |

Table on Nutrition Facts of Standardized Meals

METHODS FOR EVALUATING GLYCEMIC REGULATION AND APPLICATIONS THEREOF

CROSS REFERENCE TO RELATED APPLICATIONS

This application claims priority to U.S. Provisional Application Ser. No. 62/681,014 entitled "Methods for Evaluating Glycemic Regulation and Applications Thereof," filed Jun. 5, 2018, which is herein incorporated by reference in its entirety.

STATEMENT REGARDING FEDERALLY SPONSORED RESEARCH OR DEVELOPMENT

This invention was made with Government support under contract DK110186 awarded by the National Institutes of Health. The Government has certain rights in the invention.

FIELD OF THE INVENTION

The invention is generally directed to processes evaluation of glycemic regulation, and more specifically to methods and systems for classifying individuals based on their temporal glycemic pattern, and applications thereof, including treatments.

BACKGROUND

One in ten individuals are affected by diabetes, a condition involving abnormal regulation of glycemia (i.e., the level sugar or glucose in blood). Standard assessments of glycemia typically utilize single time-point or an average of measurements of blood glucose, without consideration for how blood glucose fluctuates over time. A few common methods to assess glycemia include measuring fasting glucose levels, measuring glycated hemoglobin (HbA1c test), and oral glucose tolerance test (OGTT).

Continuous glucose monitoring (CGM) has emerged as a method to track blood glucose levels throughout the day. Utilizing a tiny sensor inserted under an individual's skin, CGM can assess an individual's glycemic regulation trends on a temporal scale, which may fluctuate dependent on an individual's carbohydrate consumption and insulin response. CGM has provided great benefits for diabetic patients, which allows a patient to better monitor their glycemia.

SUMMARY OF THE INVENTION

A number of embodiments are directed to developing a glycemic pattern classification system using continuous glucose monitoring (CGM) data. In several embodiments, an individual can be classified using CGM data to determine her glycemic pattern. Numerous embodiments treat an individual based on her glycemic pattern classification.

Processes, in accordance with various embodiments, fragment CGM data in a number of temporally defined windows, which are in turn used to develop dissimilarity matrices between the windows. In a number of embodiments, spectral clustering is performed to generate classes of glycemic patterns. Numerous embodiments incorporate an individual's glycemic pattern into a dissimilarity matrix to perform spectral clustering to classify that individual based on their glycemic pattern.

In several embodiments, an individual is treated based on their glycemic pattern classification. A number of treatments, in accordance with various embodiments, treat an individual with medications, dietary supplements, dietary alterations, physical exercise, or any combination thereof.

In an embodiment, a first individual's continuous glucose monitoring data is fragmented into temporally defined windows. The first individual's temporally defined windows is entered into a dissimilarity matrix that has been constructed using a panel of individuals' temporally defined windows of fragmented continuous glucose monitoring data. The first individual's glycemic pattern is classified into a particular class by performing spectral clustering on the dissimilarity matrix. The spectral clustering utilizes continuous glucose monitoring data from a panel of individuals to generate a set of classes. The spectral clustering clusters the first individual and each individual of the panel into particular class of the set of classes as determined by each individual's variability in blood glucose levels. The first individual is treated based on the individual's glycemic pattern classification.

In another embodiment, the individual is treated with one of the following treatments: a medication, a dietary supplement, a dietary alteration, and physical exercise.

In yet another embodiment, the spectral clustering classifies the first individual into a class that is characterized as having greater than moderate glycemic variability. The first individual is administered a medication used to treat type II Diabetes.

In a further embodiment, the medication is one of: insulin, alpha-glucosidase inhibitors, biguanides, dopamine agonists, DPP-4 inhibitors, glucagon-like peptides, meglitinides, sodium glucose transporter 2 inhibitors, sulfonylureas, and thiazolidinediones.

In still yet another embodiment, the spectral clustering classifies the first individual into a class that is characterized as having moderate or greater than moderate glycemic variability. The first individual is administered a dietary supplement, which is one of: alpha-lipoic acid, chromium, coenzyme Q10, garlic, hydroxychalcone (cinnamon), magnesium, omega-3 fatty acids, psyllium and vitamin D.

In yet a further embodiment, the temporally defined window has length of: 0.5, 1.0, 1.5, 2.0, 2.5, 3.0, 3.5, 4.0, 4.5, or 5.0 hours In an even further embodiment, the temporally defined windows overlap to yield a coverage greater than 1×.

In yet an even further embodiment, the fragmentation of continuous glucose monitoring data is determined based upon a parameter, which is one of: cluster number, proportion of variance explained, average silhouette width, Calinski-Harabasz index, entropy, and Dunn index.

In still yet an even further embodiment, the dissimilarity matrix is calculated between all pairs of windows across the first individual.

In still yet an even further embodiment, the dissimilarity matrix is calculated using at least one of: complexity invariant distance (CID), dynamic time warping (DTW), Euclidean, and a combination of complexity invariant distance with dynamic time warping (CID-DTW).

In still yet an even further embodiment, the spectral clustering is performed using the Luxburg method.

In still yet an even further embodiment, the spectral clustering clusters individuals into at least two classes.

In still yet an even further embodiment, the spectral clustering clusters individuals into a low glycemic variability class, a moderate glycemic variability class, and a severe glycemic variability class.

In still yet an even further embodiment, the at least two classes are determined without supervision.

In still yet an even further embodiment, the first individual has not been diagnosed as diabetic or prediabetic.

In still yet an even further embodiment, the first individual has not been diagnosed as normoglycemic.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

FIG. 5 illustrates an exemplary method to classify patterns with spectral clustering and perform various applications based on the clustering results in accordance with an embodiment of the invention.

FIG. 6 provides a table on general characteristics of individuals used in glycemic panel study, used in accordance with various embodiments of the invention.

FIG. 7 provides a table on panel characteristics, separated into diabetic diagnosis cohorts, used in accordance with an embodiment of the invention.

FIG. 11 provides a table comparing common CGM metrics between glucotypes, generated in accordance with an embodiment of the invention.

FIG. 13 provides a table of correlations between each glucotype pattern and a number of clinically relevant metabolic measures, generated in accordance with an embodiment of the invention.

FIG. 15 provides a table on nutrition facts of standardized meals, utilized in accordance with an embodiment of the invention.

DETAILED DESCRIPTION

Figure 1:
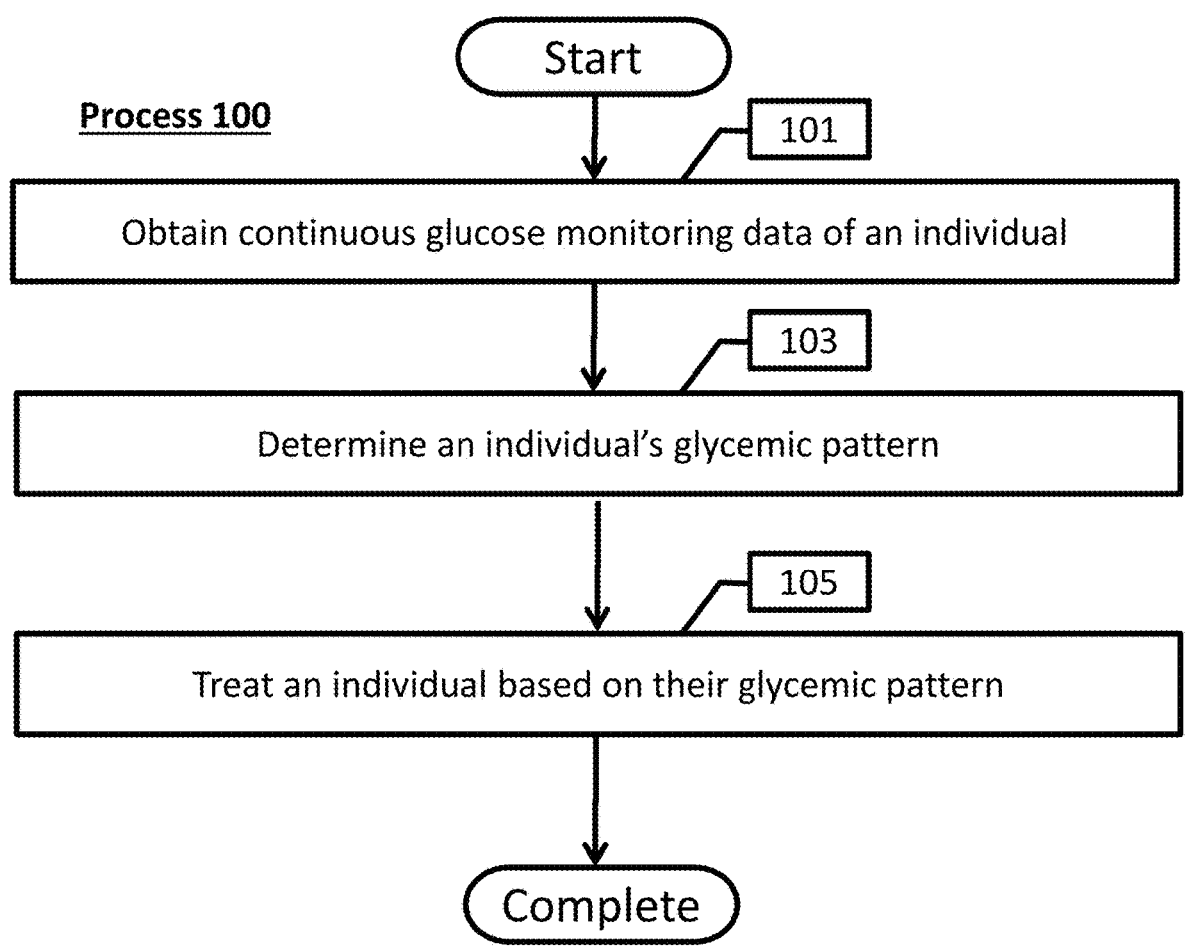
FIG. 1 illustrates a process for treating an individual based on their glycemic pattern in accordance with an embodiment of the invention.

Turning now to the drawings and data, methods and processes to classify and treat individuals having a particular glycemic pattern and applications thereof are described, in accordance with various embodiments of the invention. In several embodiments, continuous glucose monitoring (CGM) data of an individual is collected and used to classify that individual based on their glycemic pattern (an individual's classification is also referred to as "glucotype"). Many embodiments utilize an individual's classification to perform a treatment upon that individual. In some instances, a treatment can include a medication, a dietary supplement, a dietary alteration, physical exercise, and any combination thereof.

Glycemic dysregulation, especially type 2 diabetes, is one of the most significant health problems worldwide, and affects 30.2 million adults in the U.S. and 422 million worldwide with global costs in excess of $825 billion. In the U.S. alone there are 84 million individuals with prediabetes, which convert to type 2 diabetes with an annual rate of approximately 10%.

There is growing sentiment that identifying and treating individuals with prediabetes is important. Not only do individuals with prediabetes demonstrate increased incidence of diabetes complications, a major portion of prediabetic individuals are expected to develop diabetes within four years without intervention. Various studies show that medicinal and lifestyle interventions successfully prevent prediabetes conversion into diabetes. Furthermore, medicinal and lifestyle intervention per quality-adjusted life year costs are low, leading public health experts to conclude that lifestyle changes in individuals with prediabetes are cost effective and thus viable for diabetes prevention.

A number of treatments, including weight loss, exercise, specific nutrient components, and medications, would yield significant benefits to individuals with an increased risk of developing diabetes or other complications related to glycemic dysregulation. Recent studies suggest that the positive outcome of dietary intervention to lower glycemic excursions may be improved by using personalized dietary recommendations. Accordingly, various embodiments of the invention generate personalized recommendations, including treatments, to help control glycemic dysregulation and improve post-meal glucose responses.

A major complication with current metrics of glucose variability, such as HbA1c and OGTT measurements, is that they measure individual aspects of the time series data, but not entire temporal profiles. Technological advances in both wearable devices and time-series data analysis enable the characterization of glucose variability by using the shape of continuous blood glucose curve. By analyzing the shape of the continuous glucose time series data, all aspects of variability can be simultaneously compared. Accordingly, numerous embodiments are directed to a comprehensive metric of glycemic variability, which may encompass the magnitude of blood glucose fluctuations, the rate of change of glucose concentration, relative glucose concentration, and magnitude and frequency of blood glucose fluctuations. Furthermore, a number embodiments can detect glycemic dysfunction that is not appreciable by the current standard methods, such as HbA1c, OGTT, and fasting glucose tests.

Glycemic Pattern Classification Overview

An embodiment of a process to treat an individual based on their glycemic pattern is illustrated in FIG. 1. This embodiment is directed to determining an individual's glycemic pattern and applies the knowledge garnered to a treatment plan. For example, this process can be used to treat an individual having a highly variable glycemic pattern with a medication, a dietary supplement, a dietary alteration, physical exercise, and any combination thereof.

Process 100 can begin with obtaining (101) CGM data of an individual. In many instances, CGM devices are medically attached to an individual to record their continuous blood glucose level. In some embodiments, a Dexcom (San Diego, Calif.), Abbott (Abbott Park, Ill.), Tandem (San Diego, Calif.), or Medtronic (Dublin, Ireland) CGM device is used. It should be understood, however, that any appropriate CGM device capable of temporal recordation of blood glucose level can be used.

In a number of embodiments, an individual is any individual that has their blood glucose level monitored over a period a time. In some embodiments, an individual has been diagnosed as being diabetic or pre-diabetic. Embodiments are also directed to an individual being one that has not been diagnosed with a diabetic status. In some of these embodiments, the individual is normoglycemic or diagnosed as normoglycemic, as determined by classical diabetes testing, including (but not limited to) measuring fasting glucose levels, measuring glycated hemoglobin (HbA1c test), and oral glucose tolerance test (OGTT). In a number of these embodiments, normoglycemia, pre-diabetic, and diabetic assessment is determined by standards set forth by a Diabetes organization such as the American Diabetes Association. It should be understood that any generally accepted diabetic assessment can be utilized.

Utilizing the CGM data, process 100 can determine (103) an individual's glycemic pattern. In several embodiments, an individual's glycemic pattern accounts for the variability of blood glucose concentration, which can be classified. In some embodiments, an individual's glycemic pattern falls within a particular glycemic class and/or glucotype. Various embodiments develop a number of classes to describe a populations' collection of glycemic pattern. In some embodiments, glycemic pattern classes are determined empirically defined as low variability, moderate variability, and severe variability. It should be apparent to those skilled in the art that precise definition and label of glycemic pattern classes can vary, depending on the process used to develop the various classes.

Having determined an individual's glycemic pattern, the individual can be treated (105). In a number of embodiments, a treatment entails a medication, a dietary supplement, a dietary alteration, physical exercise, or any combination thereof. In some embodiments, an individual is treated by a medical professional, such as a doctor, nurse, dietician, or similar. Various embodiments are directed to self-treatment such that an individual having a particular glycemic pattern intakes a medicine, a dietary supplement, alters her diet, or physically exercises based on the knowledge of their glycemic pattern.

Glycemic Pattern Classification into Cohorts

Figure 2:
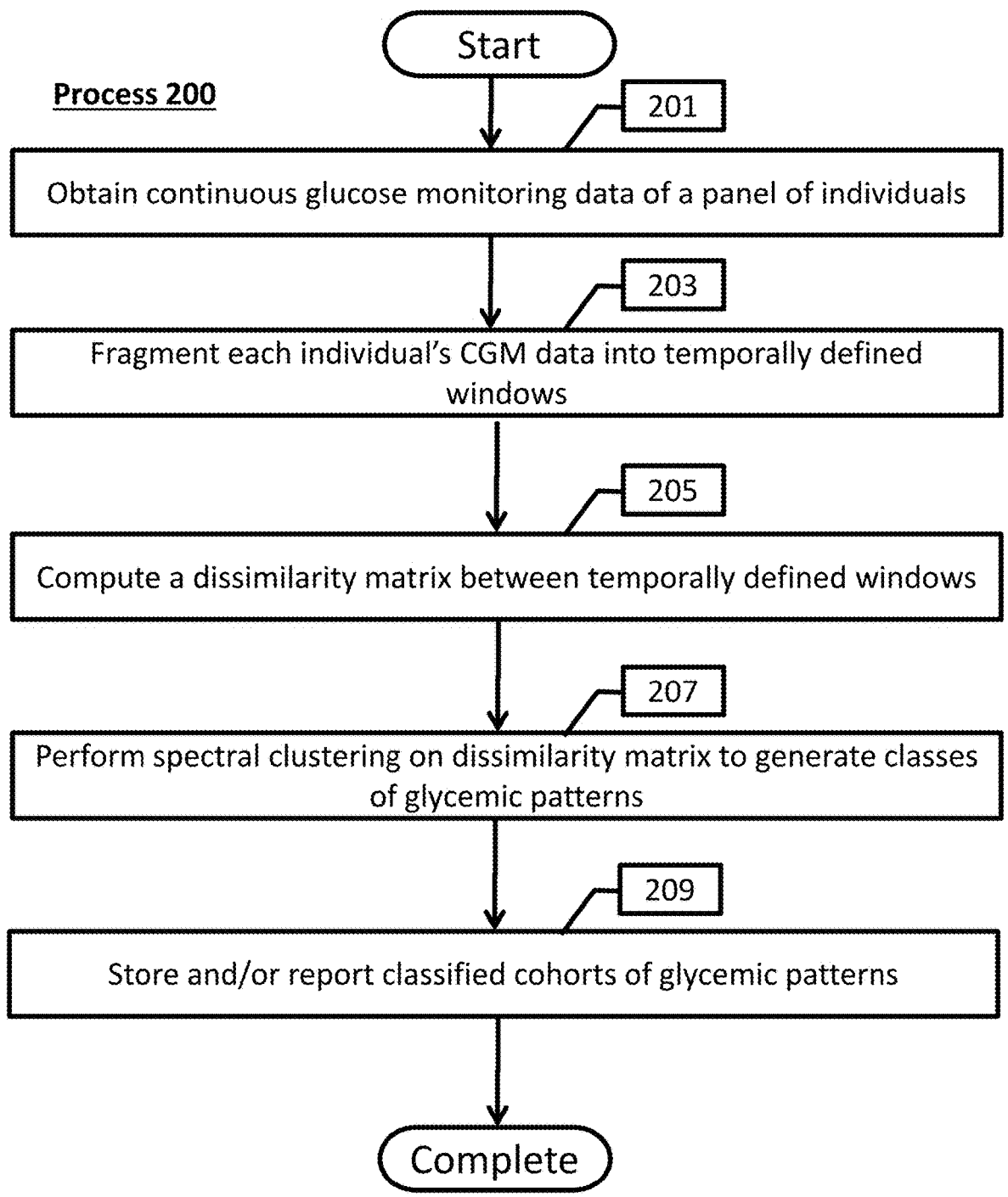
FIG. 2 illustrates a process to generate classes of glycemic patterns in accordance with an embodiment of the invention.

A process for generating classes of glycemic patterns, in accordance with an embodiment of the invention is shown in FIG. 2. Process 200 begins with obtaining (201) CGM data for a panel of individuals. In several embodiments, this CGM data is obtained from each individual of a panel and is derived from a CGM device that records blood glucose levels over a period of time.

In a number of embodiments, an individual is any individual that has their blood glucose level monitored over a period a time. In some embodiments, an individual has been diagnosed as being diabetic or pre-diabetic. Embodiments are also directed to an individual being one that has not been diagnosed with a diabetic status. In some of these embodiments, the individual is normoglycemic or diagnosed as normoglycemic, as determined by classical diabetes testing, including (but not limited to) measuring fasting glucose levels, measuring glycated hemoglobin (HbA1c test), and oral glucose tolerance test (OGTT). In a number of these embodiments, normoglycemia, pre-diabetic, and diabetic assessment is determined by standards set forth by a Diabetes organization such as the American Diabetes Association. It should be understood that any generally accepted diabetic assessment can be utilized.

In a number of embodiments, a period of time that CGM data is recorded is a day, two days, three days, a week, two weeks, a month, or longer. It should be noted that any period of time can be utilized, but longer periods of times result in more data to analyze. Furthermore, it should be noted that individuals within a panel can be monitored for different periods of times.

After obtaining CGM data from a panel of individuals, the CGM data of each individual is fragmented (203) into temporally defined windows. In a number of embodiments, the fragment window is selected from 0.5, 1.0, 1.5, 2.0, 2.5, 3.0, 3.5, 4.0, 4.5, and 5.0 hours. Various embodiments overlap fragment windows, which increases coverage of the various time frames. In some embodiments, the window overlap is selected from 25%, 50%, 55%, 60%, 65%, 70%, 75%, 80%, 85, and 90%. In several embodiments, the coverage of time frames is 1×, 2×, 3×, 4×, 5×, 10×, or more. As it would be understood by persons having skill in the art, the precise temporal window length overlap, and coverage can be selected by a number of methodologies, many of which that would be covered by various embodiments of the invention.

Many methodologies can be used to determine how to select the length, overlap, and coverage of CGM data fragmented temporal windows. In some embodiments, fragmentation is determined empirically, and/or optimized by examining a number of parameters. Parameters that can be examined, in accordance with various embodiments, include (but are not limited to) cluster number, proportion of variance explained, average silhouette width, Calinski-Harabasz index, entropy, and Dunn index. For further description and an example of optimization, see the "*Defining Glycemic Regulatory Patterns: Parameter Optimization for Clustering*" subsection as provided in the Exemplary Embodiments.

Process 200 also computes (205) a dissimilarity matrix between temporally defined windows. A dissimilarity matrix, in accordance with numerous embodiments, is a matrix of distance metrics between the temporally defined sliding windows. Multiple embodiments calculate a dissimilarity matrix between all pairs of windows across all individual. In several embodiments, a dissimilarity matrix is calculated using at least one of: complexity invariant distance (CID), dynamic time warping (DTW), Euclidean, and a combination of complexity invariant distance with dynamic time warping (CID-DTW). In some embodiments, CID-DTW is used to compute a dissimilarity matrix, which may have advantages in clustering performance and/or applicability in comparing glycemic temporal patterns. Despite only a few methods to calculate a dissimilarity matrix are described, it should be understood that any appropriate method to calculate a dissimilarity matrix for use in spectral clustering would fall within a number of embodiments of the invention.

Spectral clustering can be performed (207) on a dissimilarity matrix to generate classes of glycemic patterns (also referred to as "glucotypes"). Glycemic pattern classes, in accordance with numerous embodiments, define a cohort of individuals having a particular variability in blood glucose level. In some embodiments, a glycemic pattern variability classes are used to define cohorts. In some such embodiments, three variability classes are defined, which may be defined as low, moderate and severe.

In several embodiments, spectral clustering can be performed according the Luxburg method (see U. Von Luxburg, *Stat. Comput.* 17 (2007), the disclosure of which is herein incorporated by reference). Accordingly, in various embodiments, spectral clustering the eigenvalues (spectrum) and eigenvectors of the dissimilarity matrix are computed and only the eigenvectors corresponding to the smallest eigenvalues are considered. This allows a reduction of the dimensionality of the data before performing the clustering. Each temporal window could be seen as projected onto the lower dimensional eigenvector space. K-means clustering, in accordance with several embodiments, is then applied to the windows projected onto the space defined by the smallest k eigenvectors.

Process 200 also outputs (209) a report containing classes of glycemic patterns. As is discussed further below, these classes can be used to determine an individual's glycemic pattern, which can further used to treat the individual.

While specific examples of generating classes of glycemic patterns are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for generating classes of glycemic patterns appropriate to the requirements of a given application can be utilized in accordance with various embodiments of the invention.

Classification of an Individual's Glycemic Pattern

Figure 3:
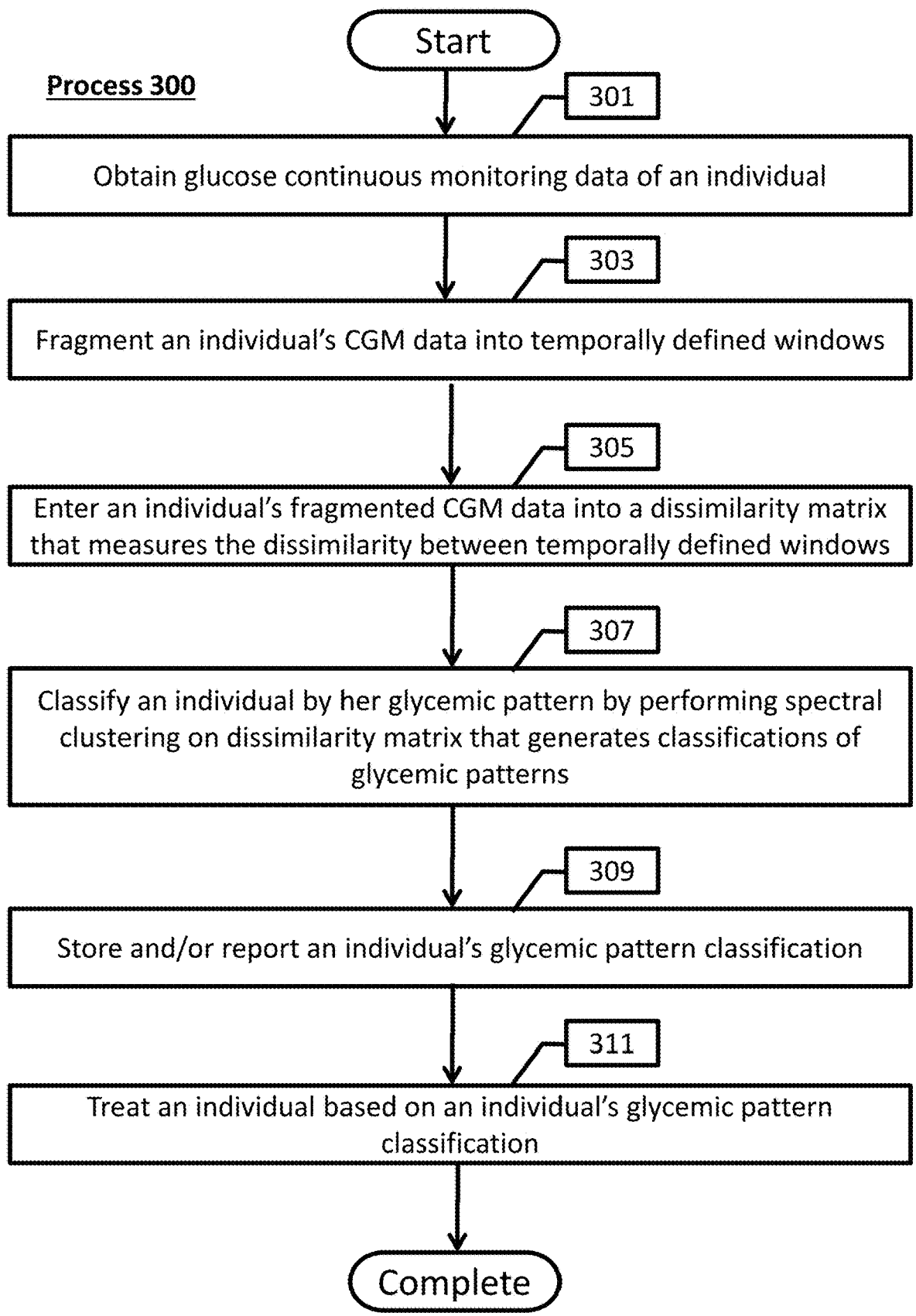
FIG. 3 illustrates a process to classify and treat an individual based on her glycemic pattern in accordance with an embodiment of the invention.

A process for classifying and further treating an individual based on their glycemic pattern in accordance with an embodiment of the invention is shown in FIG. 3. Process 300 (301) obtains continuous glucose monitoring data of an individual. In several embodiments, CGM data is derived from a CGM device that records blood glucose levels over a period of time.

In a number of embodiments, an individual is any individual that has their blood glucose level monitored over a period a time. In some embodiments, an individual has been diagnosed as being diabetic or pre-diabetic. Embodiments are also directed to an individual being one that has not been diagnosed with a diabetic status. In some of these embodiments, the individual is normoglycemic or diagnosed as normoglycemic, as determined by classical diabetes testing, including (but not limited to) measuring fasting glucose levels, measuring glycated hemoglobin (HbA1c test), and oral glucose tolerance test (OGTT). In a number of these embodiments, normoglycemia, pre-diabetic, and diabetic assessment is determined by standards set forth by a Diabetes organization such as the American Diabetes Association. It should be understood that any generally accepted diabetic assessment can be utilized.

In a number of embodiments, a period of time that CGM data is recorded is a day, two days, three days, a week, two weeks, a month, or longer. It should be noted that any period of time can be utilized, but longer periods of times result in more data to analyze.

After obtaining CGM data from an individual, the CGM data is fragmented (303) into temporally defined windows. In a number of embodiments, the fragment window is selected from 0.5, 1.0, 1.5, 2.0, 2.5, 3.0, 3.5, 4.0, 4.5, and 5.0 hours. Various embodiments overlap fragment windows, which increases coverage of the various time frames. In some embodiments, the window overlap is selected from 25%, 50%, 55%, 60%, 65%, 70%, 75%, 80%, 85%, and 90%. In several embodiments, the coverage of time frames is 1×, 2×, 3×, 4×, 5×, 10×, or more. As it would be understood by persons having skill in the art, the precise temporal window length overlap, and coverage can be selected by a number of methodologies, many of which that would be covered by various embodiments of the invention.

Many methodologies can be used to determine how to select the length overlap, and coverage of CGM data fragmented temporal windows. In some embodiments, fragmentation is determined empirically, and/or optimized by examining a number of parameters. Parameters that can be examined, in accordance with various embodiments, include (but are not limited to) cluster number, proportion of variance explained, average silhouette width, Calinski-Harabasz index, entropy, and Dunn index. For further description and an example of optimization, see the "*Defining Glycemic Regulatory Patterns: Parameter Optimization for Clustering*" subsection as provided in the Exemplary Embodiments.

Process 300 also enters (305) an individual's CGM data into a dissimilarity matrix that measures the dissimilarity between temporally defined windows. A dissimilarity matrix, in accordance with numerous embodiments, is a matrix of distance metrics between the temporally defined sliding windows. Multiple embodiments calculate a dissimilarity matrix between all pairs of windows across an individual. In several embodiments, a dissimilarity matrix is calculated using at least one of: complexity invariant distance (CID), dynamic time warping (DTW), Euclidean, and a combination of complexity invariant distance with dynamic time warping (CID-DTW). In some embodiments, CID-DTW is used to compute a dissimilarity matrix, which may have advantages in clustering performance and/or applicability in comparing glycemic temporal patterns. Despite only a few methods to calculate a dissimilarity matrix are described, it should be understood that any appropriate method to calculate a dissimilarity matrix for use in spectral clustering would fall within a number of embodiments of the invention.

In a number of embodiments, dissimilarity matrices that have been computed for a panel of individuals is utilized, such as (for example) the dissimilarity matrices described in FIG. 2.

Spectral clustering can be performed on a dissimilarity matrix having the entered CGM data of an individual to classify (307) that individual. An individual's glycemic pattern can be classified, in accordance with numerous embodiments, as having a particular variability in blood glucose level. In some embodiments, an individual may be classified into one glycemic pattern variability class of a spectrum of classes. In some such embodiments, three variability classes are defined, and an individual may be classified has having low, moderate or severe glycemic pattern variability.

In several embodiments, spectral clustering can be performed according the Luxburg method (see U. Von Luxburg, Stat. Comput. 17 (2007), the disclosure of which is herein incorporated by reference). Accordingly, in various embodiments, spectral clustering the eigenvalues (spectrum) and eigenvectors of the dissimilarity matrix are computed and only the eigenvectors corresponding to the smallest eigenvalues are considered. This allows a reduction of the dimensionality of the data before performing the clustering. Each temporal window could be seen as projected onto the lower dimensional eigenvector space. K-means clustering, in accordance with several embodiments, is then applied to the windows projected onto the space defined by the smallest k eigenvectors.

In a number of embodiments, a spectral clustering algorithm incorporates data from a panel of individuals, such as (for example) the spectral clustering algorithm described in FIG. 2. When a spectral clustering algorithm utilizes a panel of individuals, a singular individual can be classified based on the classifications generated by the spectral clustering.

Process 300 also outputs (309) a report containing an individual's classification of her glycemic pattern. Furthermore, based on an individual's glycemic pattern classification, the individual is treated (311) to ameliorate a symptom related to the glycemic pattern. In several embodiments, an individual is provided with a personalized treatment plan.

While specific examples of processes for identifying and scoring splicing events are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for identifying and scoring splicing events appropriate to the requirements of a given application can be utilized in accordance with various embodiments of the invention.

Systems of Glycemic Pattern Classification

Figure 4:
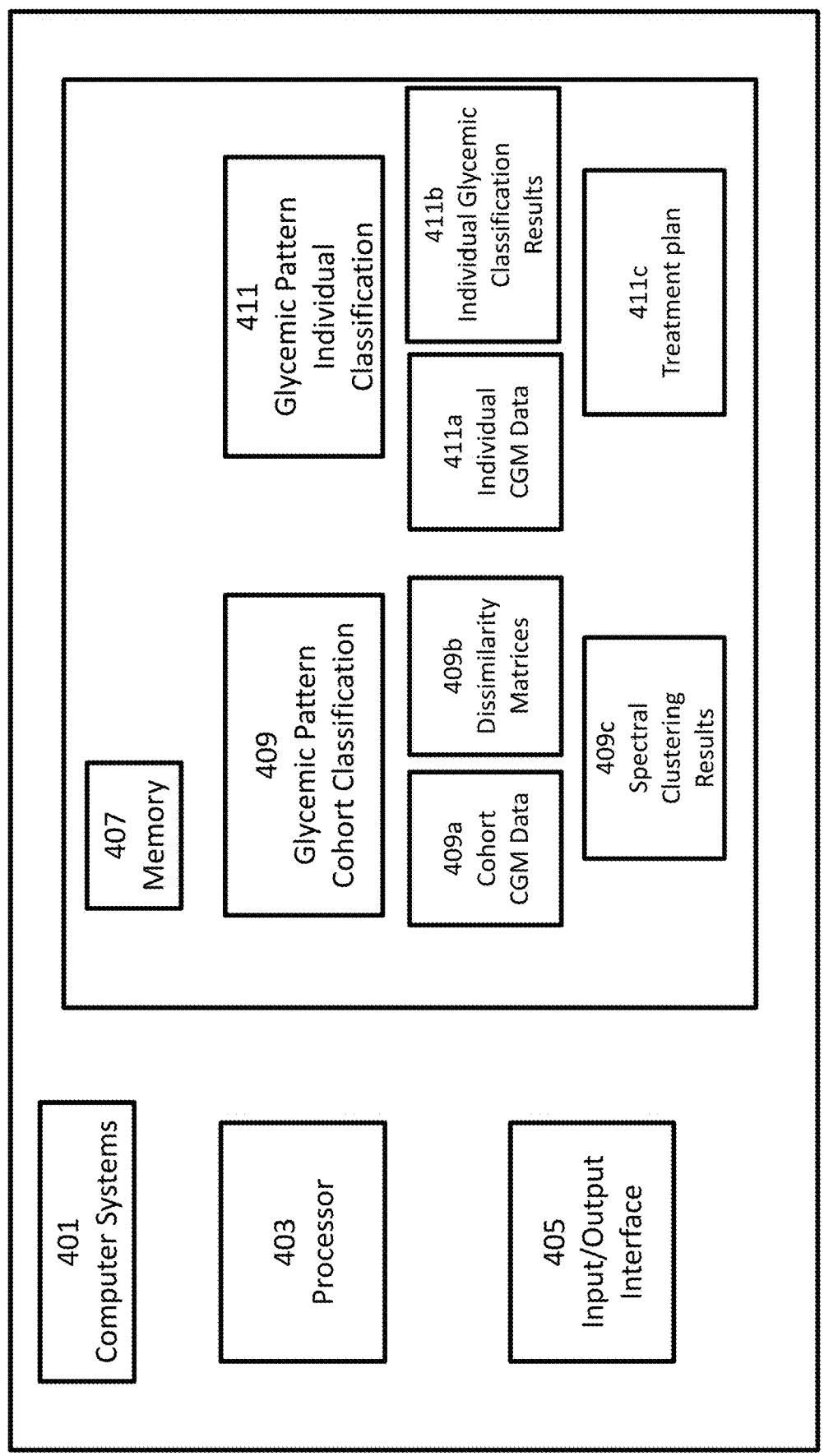
FIG. 4 illustrates a diagram of computing systems configured to classify individuals based on their glycemic pattern in accordance with various embodiments of the invention.

Turning now to FIG. 4, computer systems (401) may be implemented on a set of one or more computing devices in accordance with some embodiments of the invention. The computer systems (401) may incorporate a personal computer, a laptop computer, and/or any other computing device with sufficient processing power for the processes described herein. The computer systems (401) include a processor (403), which may refer to one or more devices within the set of computing devices that can be configured to perform computations via machine readable instructions stored within a memory (407) of the computer systems (401). The processor may include one or more microprocessors (CPUs), one or more graphics processing units (GPUs), and/or one or more digital signal processors (DSPs). According to other embodiments of the invention, the computer system may be implemented on multiple computers.

In a number of embodiments of the invention, the memory (407) may contain a glycemic pattern cohort classification application (409) and a glycemic pattern individual classification application (411) that performs all or a portion of various methods according to different embodiments of the invention described throughout the present application. As an example, a processor (403) may perform a method similar to any of the processes described herein, during which memory (407) may be used to store various intermediate processing data such as cohort CGM data (409a), dissimilarity matrices (409b), spectral clustering results (409c), individual CGM data (411a), individual glycemic classification results (411b), and treatment plans (411c).

In some embodiments of the invention, the computer systems (401) may include an input/output interface (405) that can be utilized to communicate with a variety of devices, including but not limited to other computing systems, a projector, and/or other display devices. As can be readily appreciated, a variety of software architectures can be utilized to implement a computer system as appropriate to the requirements of specific applications in accordance with various embodiments of the invention.

Although computer systems and processes for classifying individual's glycemic pattern and performing treatment based thereon are described above with respect to FIG. 4, any of a variety of devices and processes for data associated with glycemic pattern classification as appropriate to the requirements of a specific application can be utilized in accordance with many embodiments of the invention.

Applications of Glycemic Pattern Classification

Various embodiments are directed to development of treatments related to glycemic pattern classifications. As described herein, an individual may be classified as having a particular glycemic pattern. Based on their glycemic pattern classification, individuals with high glycemic variability can be treated with various medications, dietary supplements, dietary alterations, and physical exercise regimens.

Medications and Supplements

Several embodiments are directed to the use of medications and/or dietary supplements to treat an individual based on their glycemic pattern classification. In some embodiments, medications and/or dietary supplements are administered in a therapeutically effective amount as part of a course of treatment. As used in this context, to "treat" means to ameliorate at least one symptom of the disorder to be treated or to provide a beneficial physiological effect. For example, one such amelioration of a symptom could be a reduction of glycemic pattern variability. Assessment of glycemic pattern variability can be performed in many ways, including, but not limited to assessing the changes in variability of an individual's CGM data.

A therapeutically effective amount can be an amount sufficient to prevent reduce, ameliorate or eliminate the symptoms of diseases or pathological conditions susceptible to such treatment, such as, for example, diabetes, heart disease, or other diseases that are affected by unstable glycemia. In some embodiments, a therapeutically effective amount is an amount sufficient to reduce the variability of an individual's CGM data.

A number of medications are available to treat unstable glycemia, such as those used to treat type II Diabetes. Medications include (but are not limited to) insulin, alpha-glucosidase inhibitors (e.g., acarbose, miglitol), biguanides (e.g., metformin), dopamine agonists (e.g., bromocriptine), DPP-4 inhibitors (e.g., alogliptin, linagliptin, saxagliptin, sitagliptin), glucagon-like peptides (e.g., albiglutide, dulaglutide, exenatide, liraglutide), meglitinides (e.g., nateglinide, repaglinide), sodium glucose transporter 2 inhibitors (e.g., dapagliflozin, canagliflozin, empagliflozin), sulfonylureas (e.g., glimepiride, gliclazide, glyburide, chlorpropamide, tolazamide, tolbutamide), and thiazolidinediones (e.g., rosiglitazone, pioglitazone). Accordingly, an individual may be treated, in accordance with various embodiments, by a single medication or a combination of medications described herein. Furthermore, several embodiments of treatments further incorporate heart disease medications (e.g., aspirin, cholesterol and high blood pressure medications), dietary supplements, dietary alterations, physical exercise, or a combination thereof.

Numerous dietary supplements may also help to treat unstable glycemia. Various dietary supplements, such as alpha-lipoic acid, chromium, coenzyme Q10, garlic, hydroxychalcone (cinnamon), magnesium, omega-3 fatty acids, psyllium and vitamin D have been shown to have beneficial effects on individuals having diabetes and cardiac conditions. Thus, embodiments are directed to the use of dietary supplements, included those listed herein, to be used to treat an individual based on her glycemic pattern classification. A number of embodiments are also directed to combining dietary supplements with medications, dietary alterations, and physical exercise to reduce glycemic variability.

Accordingly, in various embodiments, an individual classified as having greater than moderate (e.g., high or severe) glycemic variability is treated with a medication. In some embodiments, an individual classified as having moderate or greater than moderate glycemic variability is further monitored and/or treated with dietary supplements. In addition, in various embodiments, when an individual has been treated with a medication improves to moderate or low glycemic variability, that individual can be taken off the medication and further monitored and/or treated with dietary supplements.

Diet and Exercise

Numerous embodiments are directed to dietary alteration and exercise treatments. Altering one's lifestyle, including physical activity and diet, has been shown to improve glycemic regulation. Accordingly, in a number of embodiments, an individual is treated by altering their diet and increasing physical activity in response to a classification to their glycemic regulatory pattern.

There are various diets that will help different individuals in getting better glycemic control. A number of embodiments are directed to treatments to reduce weight, which has been considered by some best approach to control one's glycemia. There are many programs based on the seminal study for a low fat diet to prevent diabetes (see Diabetes Prevention Program (DPP) Research Group. *Diabetes Care.* 2002 25:2165-71). For others, a diet low in refined carbohydrates and sugars will work better. Numerous embodiments take a more personalized approach such that one can utilize the CGM results to determine which foods that causing glycemic spikes for an individual and devise a diet to limit these particular foods while maintaining appropriate nutrient intake. Numerous embodiments are directed to treating an individual by substituting saturated fats with monounsaturated and unsaturated fats to help lower the risk for cardiovascular disease, which would be beneficial for many individuals struggling to control their glycemic pattern. Also, embodiments are directed to increasing amounts of fiber in the diet, which would be highly recommended to both help with glycemic control and also balance serum lipid levels (cholesterol and triglycerides).

Exercise has a large impact on glycemic control. In several embodiments, a treatment would entail a minimum of some minutes of active exercise per week. In some embodiments, treatments would include a minimum of 150 minutes of exercise a week, however, the precise length of exercise may be dependent on the individual to be treated and their cardiovascular health. It is further noted that cardiovascular exercise is important for the immediate glycemic control and weight training will have a long-term effect by increasing muscle mass, affecting glucose utilization during rest.

In many embodiments, a treatment to help control glucose levels is stress management, as stress increases blood glucose levels. Some proven ways to help control stress include meditation, social support, adequate sleep, journaling, and therapy.

EXEMPLARY EMBODIMENTS

Bioinformatic and biological data support the methods and systems of classifying individuals based on glycemic regulation and applications thereof. In the ensuing sections, exemplary computational methods and exemplary applications related to classifying individuals based on glycemic regulation are provided.

Identification of Glycemic Regulation Patterns

In an exemplary embodiment, a new measure of glucose variability was derived from the spectral clustering of glycemic signatures using time-series-specific distance metrics. This method can be used to define a clinically relevant metric of glycemic patterns that would classify individuals into different glycemic pattern regulation classes, which is referred to throughout as glucotypes. A summary metric of glucose variability that encompasses all components of glucose signatures should provide a more comprehensive, dynamic and granular understanding of diabetes etiology, to detect glucose dysregulation at earlier stages of disease, and provide a tool by which one can personalize treatment for optimal glucose response. This exemplary methodology identified many individuals not known to be pre-diabetic by standard measures (fasting glucose, oral glucose tolerance test (OGTT) and HbA1c) to have high levels of postprandial glucose similar to pre-diabetics and diabetics. Although postprandial spikes in glucose have been reported previously, the discovery of these in patients that had been demonstrated to be normal by OGTT and insulin resistant individuals was unexpected; Deep phenotyping of participants for different measures of glucose dysfunction further enabled the development of models for glucose dysregulation at an individual level.

Panel Recruitment and Characteristics

In this exemplary implementation of glucotype classification, 57 healthy participants without prior diagnosis of diabetes were recruited. The panel was composed of 32 females and 25 males, with an age range of 25 to 76 (median 51). The study was approved under IRB 37141 and written consent was obtained for all participants.

Human subjects were recruited from the San Francisco Bay Area via local newspaper advertisements and informational lectures to the community. All subjects provided written, informed consent and the protocol was approved by the Stanford Internal Review Board. Subjects were required to be healthy and free of major organ disease, chronic inflammatory conditions, malignancy, uncontrolled hypertension, eating disorder, history of bariatric surgery, diagnosis of diabetes, use of weight loss or diabetogenic medications, or recent unstable weight. Screening and eligibility determination was conducted in the Stanford Clinical Translational Research Unit (CTRU), with history and physical exam, fasting plasma glucose and HbA1c.

The blood glucose of each participant was monitored using CGM in their normal environment. The participants were extensively characterized with clinical metabolic phenotypes (see FIG. 5). Dexcom G4 CGM devices, which provide interstitial glucose concentrations every five minutes, were placed on participants in the Stanford CTRU and worn by participants for a minimum of two weeks and maximum of four weeks during a period of stability in their lifestyle (no vacations, holidays, festivities, etc.). Participants were instructed to calibrate monitors once to twice daily using glucose meters (AccuCheck Nano SmartView). Subjects were blinded to the results of monitoring until after the monitors were removed so that their dietary habits were not influenced by the glucose recordings.

Glucose tolerance of each participant was assessed after an overnight fast via oral glucose tolerance test (OGTT) with plasma samples drawn for measurement of glucose (oximetric method) and insulin (radioimmunoassay) at baseline, 30 minutes and 120 minutes after administration of 75 grams of glucose. From the baseline sample hemoglobin A1C (HbA1c), triglyceride, and high-density lipoprotein cholesterol levels were also determined. Insulin-mediated glucose uptake was quantified via a steady-state plasma glucose test. Insulin secretion was calculated from the OGTT as per below. The tests were usually performed when the participants were not wearing the Dexcom device.

Insulin secretion rate was estimated from C-peptide concentration measured during OGTT tests, at baseline, 30 minutes and 120 minutes after administration of 75 grams of glucose. The Insulin SECretion (ISEC) software was used to calculate pre-hepatic insulin secretion from plasma C-peptide measurements with adjustment for age, sex, and BMI (for more on ISEC software, see R. Hovorka, P. A. Soons, & M. A. Young Comput. Methods Programs Biomed. 50, 253-264 (1996), the disclosure of which is herein incorporated by reference). The ISEC software can be obtained from the author Roman Hovorka, PhD, Metabolic Modelling Group, Centre for Measurement and Information in Medicine, Department of System Science, City University, Northampton Square, London EC1V OHB, United Kingdom. An error coefficient of variation of 5% and 15 minutes intervals was required.

On screening tests, five met criteria for having type 2 diabetes, in accordance with the American Diabetes Association definitions, which is defined as HbA1c≥6.5%, fasting blood glucose ≥126 mg/dL, or 2 hour glucose during 75 gram OGTT≥200 mg/dL. Fourteen had prediabetes, defined as HbA1c≥5.7% and <6.5%, fasting blood glucose in the range of 100-125 mg/dL, or two-hour glucose during OGTT in the range of 140-199 mg/dL. The remainder of the panel were normoglycemic, defined as plasma glucose and HbA1c below the above diagnostic thresholds for prediabetes and diabetes (see tables with FIGS. 6 and 7 for details on the panel). For the panel as a whole, the mean fasting glucose was 93 mg/dL, 2 hour glucose 125 mg/dL and HbA1c≥5.4%. Insulin resistance, quantified by the steady-state plasma glucose (SSPG) test, in which a higher value indicates relative resistance to insulin-mediated glucose uptake, ranged from 45 mg/dL to 335 mg/dL, reflecting great heterogeneity in the panel. This measure was particularly variable among the normoglycemic and pre-diabetic group.

Thirty subjects completed a standardized meal testing portion of the study (for details, see below). Characteristics of this panel mirrored the original panel: 20 females and 10 males, with age ranging from 25 to 65, of which 3 and 7 individuals were diagnosed with diabetes and prediabetes respectively. While eating these meals, participants wore the Dexcom monitors to record their glucose concentration before, during, and after eating the meal. Participants were instructed to eat each of these meals twice, on two separate days, and to record the time of their meals. Several participants neglected to record the time or had additional food with the standardized meals and were excluded from the analysis.

Defining Glycemic Regulatory Patterns: Data Collection

Each member of the panel wore continuous glucose monitors to record their temporal blood glucose levels. Data was extracted directly from the Dexcom G4 CGM system worn by participants. Potential glycemic signatures were generated from overlapping windows.

Figure 8:
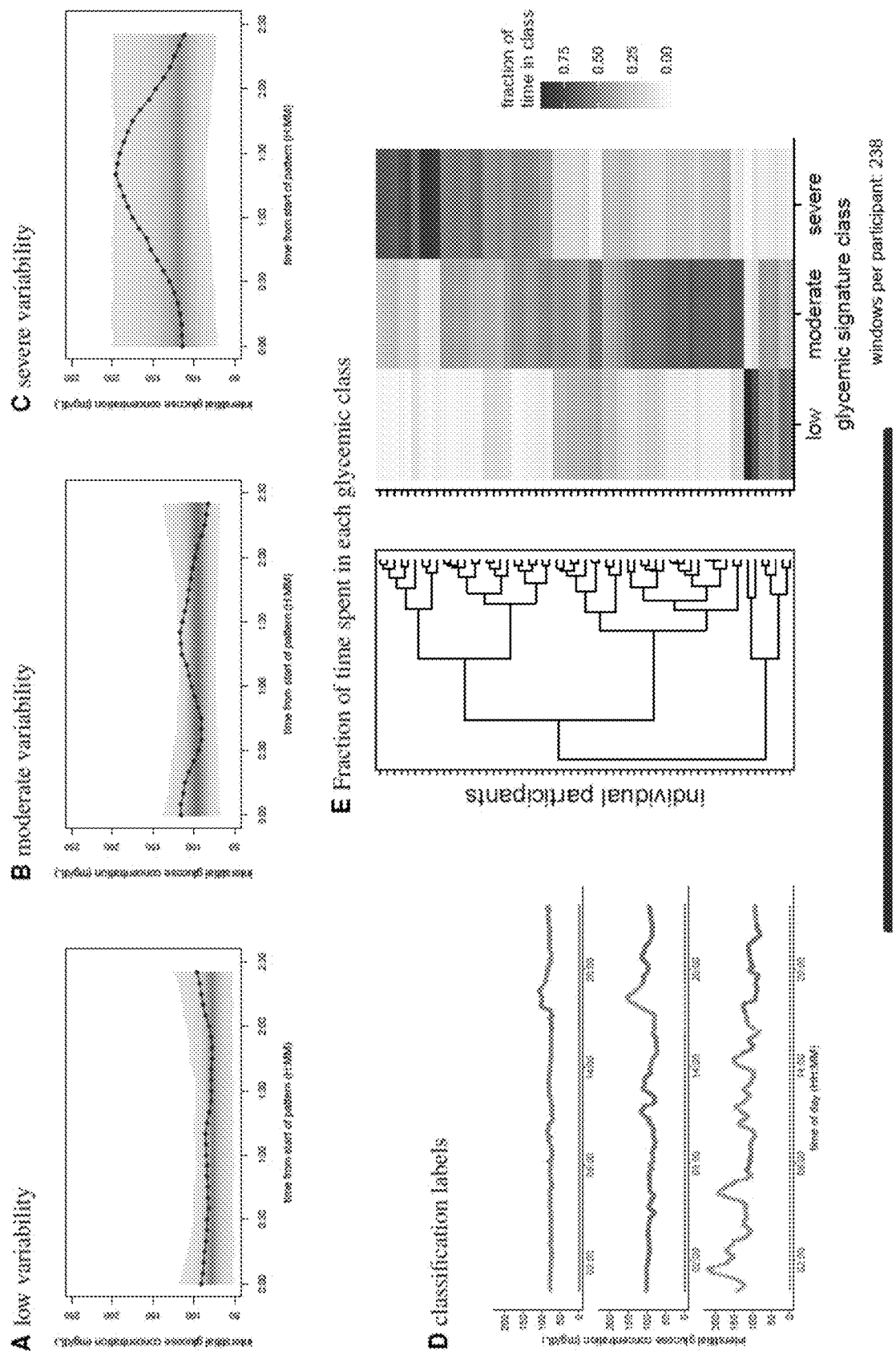
FIG. 8 illustrates CGM data and glycemic pattern classification in accordance with an embodiment of the invention.

Linear imputation for gaps under 15 minutes in length was performed in order to reduce the amount of missing data. Windows with larger gaps were excluded from the analysis. Each of these windows was then smoothed using a polynomial smoothing and z-score normalized prior to clustering. The number of windows was then normalized between participants by taking the first N windows from the start of the CGM data, where N was the smallest number of windows for a single participant. The clustering is performed on CGM data from all participants at once, including also the ones who did not eat the standardized meals or for which OGTT data was not available. Visual inspection of CGM glucose levels of 57 participants revealed highly variable intra- and interpersonal patterns of fluctuation (FIG. 8).

Defining Glycemic Regulatory Patterns: Parameter Optimization for Clustering

Figure 9:
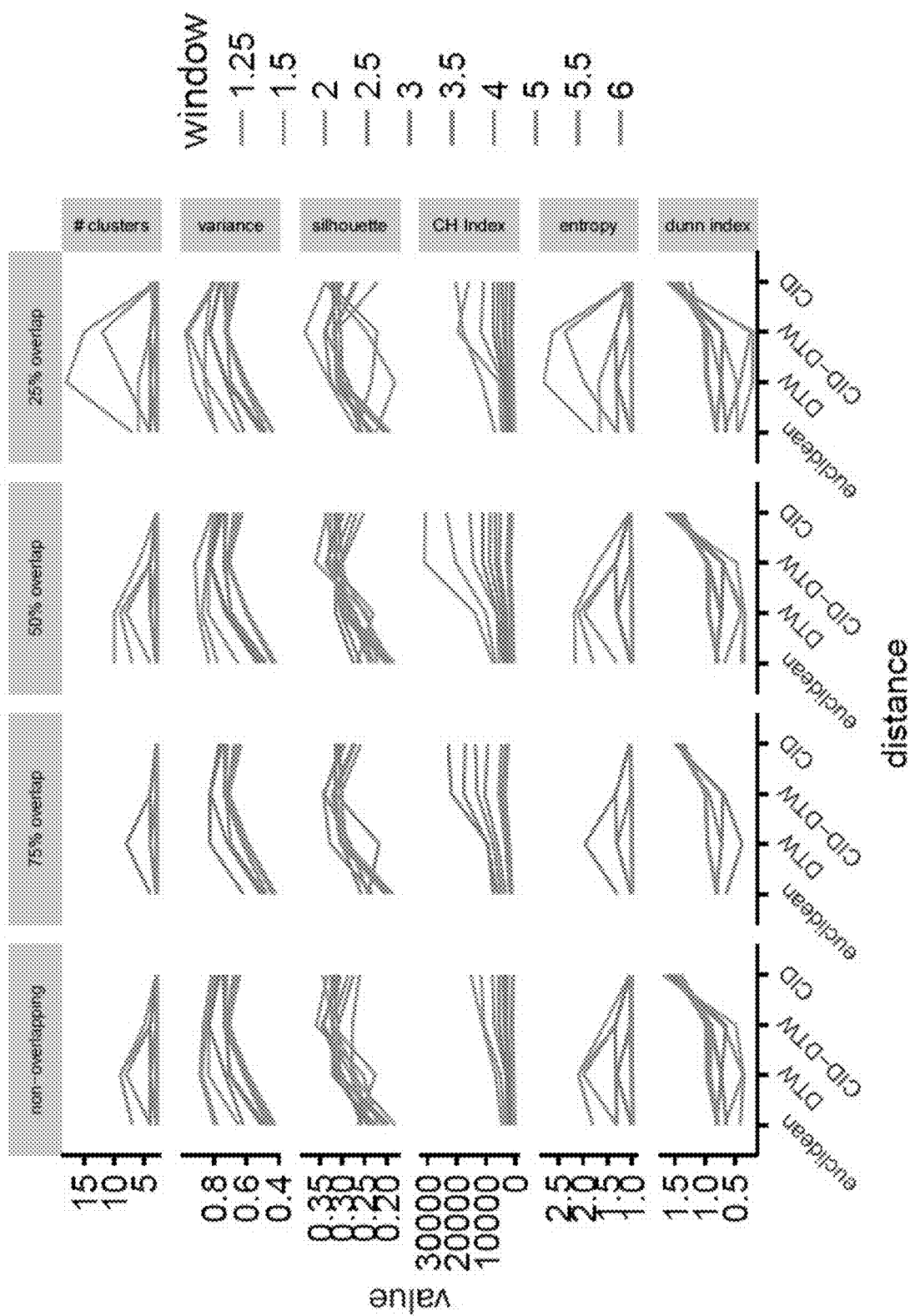
FIG. 9 provides results of various distance metrics used to measure variability, generated in accordance with an embodiment of the invention.

In an attempt to systematically capture and classify the magnitude and degree of glucose variability, the temporal profiles of blood glucose responses of the 57 participants were clustered, testing a variety of approaches, parameters and distance metrics (FIG. 9). The number of clusters used for parameter optimization is the optimal k from the eigengap heuristic, which corresponds to the distance between consecutive eigenvalues of the spectral clustering. The optimal number of clusters k could vary between different combinations of parameters, and the clustering metrics are computed with respect to a given k for each set of parameters. The optimization of window size and window overlap was based on several clustering metrics (FIG. 9):

Number of clusters: the optimal number based on the eigengap heuristic

Proportion of variance explained: total between-cluster sum-of-square (totBSS) divided by total sum-of-square (totSS). The sum-of-squares were computed on a given distance matrix with the function css( ) from the R package GMD.

Average silhouette width: The silhouette value is a measure of how similar a window is to its own cluster compared to other clusters. The silhouette index is the average of the silhouette values for all windows. For a window w, the silhouette is defined as $$s(w) = \frac{b(w) - a(w)}{\max(a(w), b(w))},$$

where b(w) is the lowest average distance of w to all points in any other cluster, of which w is not a member, and a(w) the average distance of w with all other windows within the same cluster.

Calinski-Harabasz (CH) index: ratio between total between-cluster sum-of-square (totBSS) and total within-cluster sum-of-square (totWSS) normalized by the number of windows and number of clusters. Higher CH index means better cluster definition.

Entropy: similar to the information entropy, it indicates how evenly the windows are assigned to the clusters. Low entropy means unbalanced clusters. Formally, entropy=$-\Sigma_{i=1}^{k} p_i * \log(p_i)$, where $$p_i = \frac{size_i}{W}, p_i > 0,$$

k is the number of clusters and W is the total number of windows.

Dunn index: given a certain distance metric between two clusters, it is defined as the ratio between the minimum pairwise distance over all pairs of clusters and the maximum within-cluster distance (cluster diameter) over all clusters. For a given assignment of clusters, a higher Dunn index indicates better clustering.

The average silhouette, CH index, entropy and Dunn index were computed with the function cluster.stats( ) from the R package fpc (see C. Henning, https://cran.r-project.org/package=fpc).

The same set of clustering quality metrics was used to select complexity-invariant distance dynamic time warping (CID-DTW) as distance metrics between windows. The other distances tested were Euclidean, dynamic time warping (DTW) and complexity invariant distance (CID). CID-DTW was chosen both because of its clustering performance and applicability in comparing glycemic temporal signatures.

A window size of 2.5 hours, the approximate time to respond to a meal, was chosen based on both a systematic analysis of its frequency in the power spectrum and its relevance in diabetes. After parameter optimization with a selection of overlaps, the optimal overlap was chosen to be 75%, providing a 4x coverage of each data point.

Defining Glycemic Regulatory Patterns: Spectral Clustering

Figure 10:
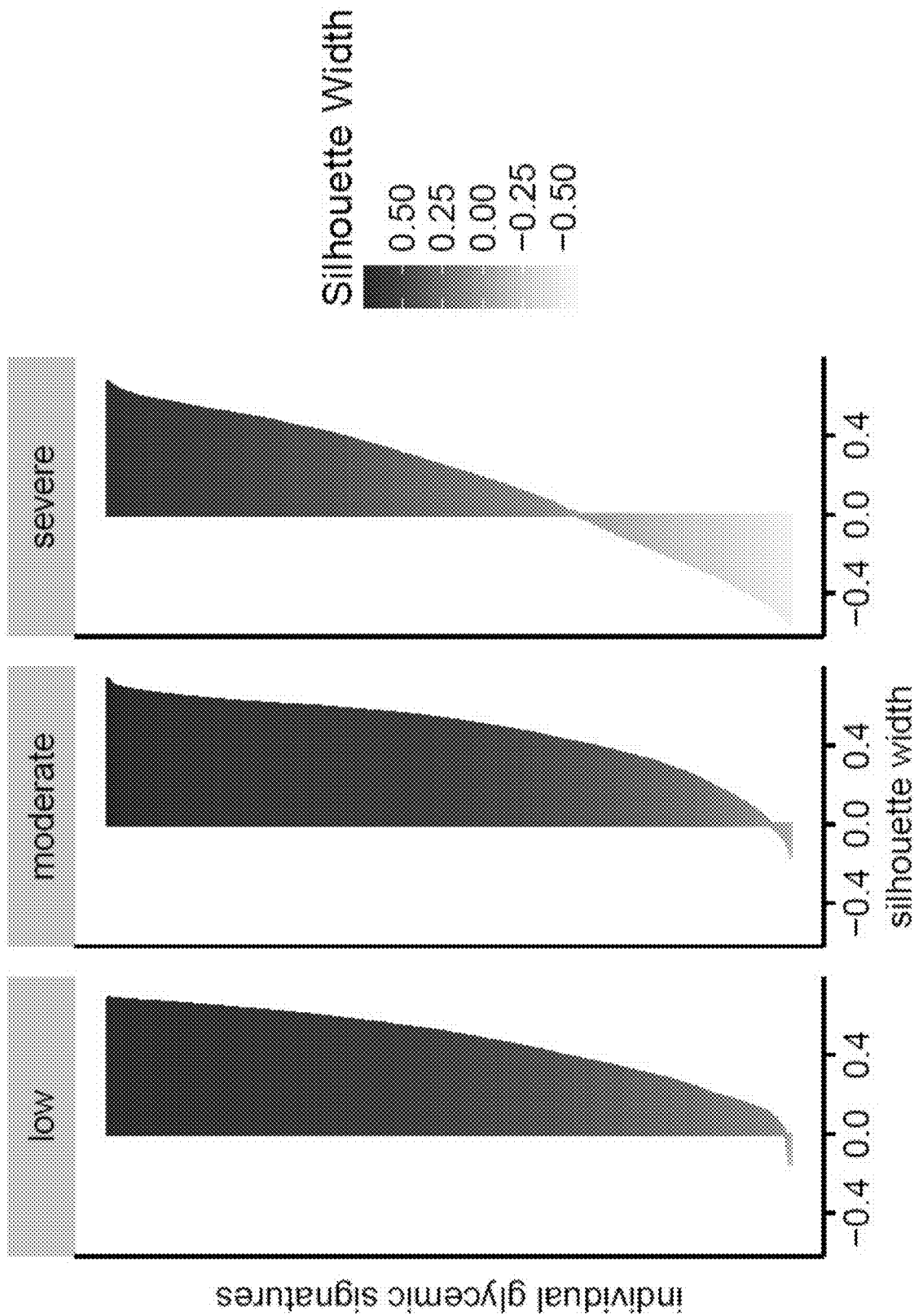
FIG. 10 provides a silhouette width results of glycemic pattern classifications, generated in accordance with an embodiment of the invention.

As described in the preceding section, the temporal profiles of each participant were segmented into sliding windows of 2.5 hours, with a 75% overlap. Complexity invariant dynamic time warping was used to compute a dissimilarity matrix between each pair of windows. By applying spectral clustering on this dissimilarity matrix, three clusters of glucose patterns emerged (low, moderate, and severe variability). Dynamic time warping to compute distances between time windows exploits the temporal nature of the data and captures high similarities between windows with similar profiles even when they are shifted. As such, this method was successful in capturing 73% of the variance. Silhouette analysis indicated a good fit for most of the windows to the groups identified by the spectral clustering (FIG. 10).

Spectral clustering was performed according to the methods in von Luxburg's tutorial on spectral clustering on the dissimilarity matrix consisting of pairwise CID-DTW distance between all pairs of windows across all individuals (see U. Von Luxburg, *Stat. Comput.* 17 (2007), the disclosure of which is herein incorporated by reference). A symmetric step pattern and Sakoe-Chiba band with a size of 10% the window size were used. The distance matrix was generated using the 'DTW' and 'Proxy' package in R (see T. Giorgino, et al., *J. Statistical Softw.* 31, 1-24 (2009); and D. Meyer & C. Buchta *R. Packag.* 1-10 (2017); the disclosures of which are herein incorporated by reference).

The number of neighbors for building the graph for the k-nearest-neighbor affinity matrix (also referred to as the adjacency graph) was optimized by finding the smallest n such that the entire graph was connected. In order to optimize this parameter, the affinity matrix and the unnormalized laplacian were calculated for several n and the smallest n was chosen such that a single eigenvalue from the unnormalized laplacian was zero.

Clustering was attempted for k−5 to k+5 (where k is the optimal number of clusters from the eigengap heuristic) with the bounds that k must be greater than two and less than half the number of windows. An ANOVA analysis was performed to determine the parameters that optimized optimal explained-variance and Calinski-Harabasz indices. The optimal number of clusters (k) was chosen after considering the elbow-method, CH index, average silhouette index, and the eigengap heuristic.

Defining Glycemic Regulatory Patterns: Analysis and Results

During clustering, each glycemic signature maintained an identifier noting the original participant and starting time. As such, glycemic signatures could easily be linked to participant, time, and glucose concentration. The portion of time spent in each class was estimated by calculating the fraction of a participant's windows assigned to the class.

The analysis revealed that the three types of patterns captured features beyond absolute glucose value, including overall variability and the dynamics of increase and decrease in slope (FIG. 8A-8D). Using the spectral clustering method, based on the amount of variability exhibited in glucose levels, the three patterns were classified as low, moderate and severe variability. These groups show a progressive increase in both the severity and magnitude of the variability in glucose concentration. It was determined that the fraction of time each participant spent in each pattern and found that some participants stayed predominantly in the low variability range whereas others were predominantly in the moderate and severe variability range (FIG. 8E), with other clear intermediates as well.

Each participant was assigned to a "glucotype" based their most frequent variability pattern: low variability (glucotype L), moderate variability (glucotype M), and severe variability (glucotype S).

The classification of glycemic patterns is consistent with differences in common metrics of glycemic variability based on an ANOVA analysis (See Table in FIG. 11). In addition, the mean variability values for these metrics increased from low, moderate, to severe glucotype, supporting classification based on increasing variability. Note that the classes increase in both variability and mean glucose concentration (77, 96 and 122 mg/dL in low, moderate and severe classes, respectively), making them a more comprehensive metric of glycemic state.

Defining Glycemic Regulatory Patterns: Classification of New Glycemic Windows

For most of this study a limited number of temporal windows (238 per person) were analyzed to ensure the same duration of glucose recordings across all individuals, unless specified otherwise. Nonetheless, spectral clustering can be also used to classify CGM profiles that were not included in the initial clustering. This approach can be used to classify individuals by entering in their CGM data into the spectral clustering.

To classify new windows it is important that the data is processed similarly to the training set. Here, the initially clustered windows are referred to as training set or training windows (238 windows per person). Specifically, the glucose values are mean-centered and scaled by using precomputed mean and standard deviation from the training windows. Any new CGM profile is fragmented into temporal windows of a similar same size as the training set (e.g., 2.5 hours) in order to have a better accuracy of the computed dynamic time warping distance. The overlap between the windows can be variable.

Because of the nature of the algorithm, dynamic time warping is a computationally intensive distance metric, therefore the computation was restricted to only a minimal subset of the training windows. It was required that a minimum of 200 training windows in total across all patients, and more training windows were add when the number of windows to classify exceeds 200. In the latter case, the number of training windows is the same as the number of windows to classify. To ensure this subset of training windows recapitulates the overall distribution of glycemic variations, the training windows are randomly selected—with a fixed random seed—based on their density distribution around the centroids of the three defined classes in the eigenvector space.

Complexity invariant dynamic time warping is then computed between each pair of new windows and randomly selected training windows. This distance matrix is converted to an affinity matrix following the implementation of an affinityMatrix( ) function in a Similarity Network Fusion R package. The sigma parameter of the affinityMatrix( ) function is the precomputed estimate based on the entire training set. The new windows in the affinity matrix are projected onto the eigenvector space derived from the randomly selected windows of the training set, and individually normalized across the eigenvectors. Finally, the windows in the eigenvector space are assigned to a glycemic signature class according to the class of the closest centroid.

To check the reliability of this approach all the windows in the training set were classified and achieved a remarkable accuracy of 95%. It is important to note that the 3 glucotype classes that were defined are the results of an unsupervised method. Since there is no ground truth training labels, performance optimization strategies were not implemented at this point.

Correlation of Glycemic Regulatory Patterns with Clinical Metabolic Parameters

Figure 12:
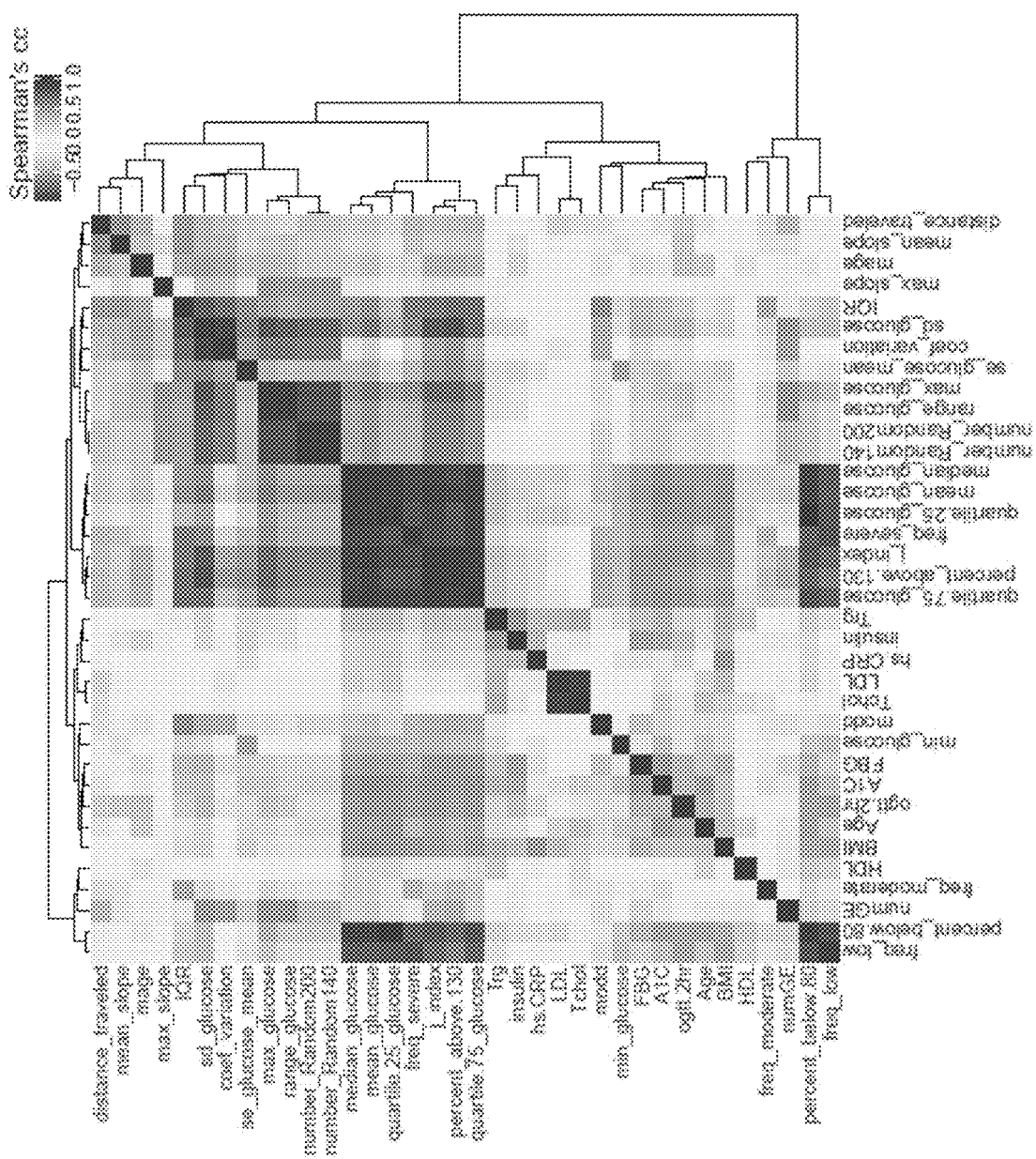
FIG. 12 provides results of a spearman's correlation between each glucotype pattern and a number of clinically relevant metabolic measures, generated in accordance with an embodiment of the invention.

To further verify the glycemic pattern classifications of the low, moderate, and severe, the fraction of time spent in each glucotype pattern was correlated with a number of clinically relevant metabolic measures (FIGS. 12 and 13). These metrics included descriptive statistics measures such as mean/min/max glucose concentration, mean/max rate of change, interquartile range, and standard deviation. Other metrics included mean amplitude of glycemic excursion (MAGE), distance traveled, J index, and coefficient of variation. Mean amplitude of glycemic excursion was also calculated.

Figure 14:
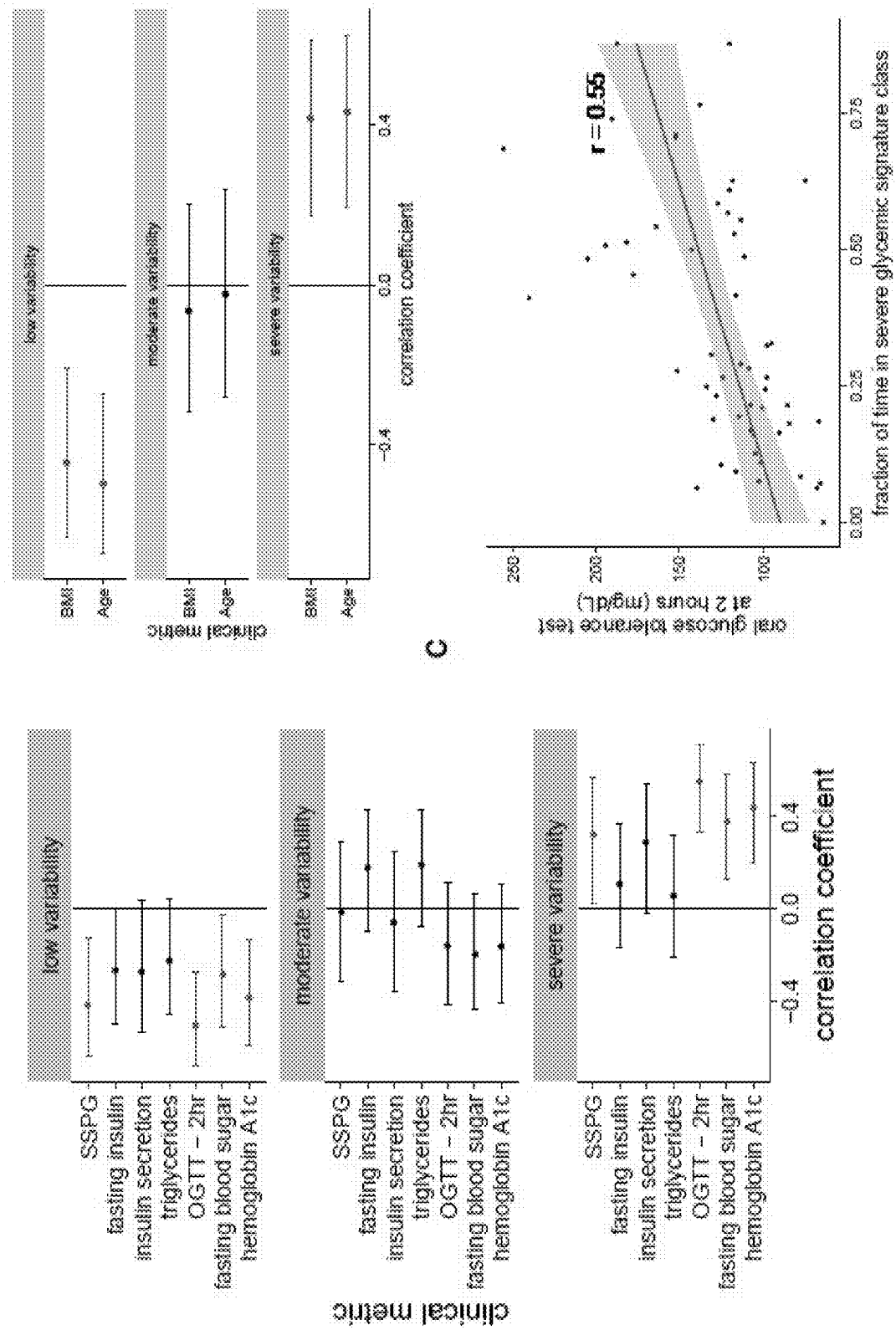
FIG. 14 provides results of a correlation between glycemic pattern classifications and measures of glucose homeostasis, generated in accordance with an embodiment of the invention.

The results indicated significant positive correlations (P<0.05) between the time spent in low glycemic signatures and lower values for fasting glucose, HbA1c, OGTT, SSPG, BMI and age (FIG. 14). Similarly, the frequency of time spent in severe glycemic signatures was associated with higher values for fasting glucose, HbA1c, OGTT and SSPG, BMI and age (FIG. 14).

Forest plots and correlations were performed using a two-sided Pearson's product-moment correlation. Values reported are 95% confidence interval. A non-parametric Kruskal-Wallis rank sum test was used to compare the average values of common variability metrics for the glycemic signatures in each class. P-values are reported. Multiple hypothesis testing was performed using the Benjamini Hochberg method. A principal component analysis was performed to assess the separation by dominant glycemic signature class and current diagnostics. The features for the analysis included clinical tests and CGM metrics commonly used to assess blood sugar control: age, body mass index, HbA1c, fasting blood sugar, OGTT—2 hr, fasting insulin, high sensitivity CRP, total cholesterol, triglycerides, high-density lipoprotein, low density lipoprotein, mean glucose, standard deviation glucose, range of glucose, min glucose, max glucose, glucose 25% quantile, median glucose, glucose 75% quantile, mean rate of change, max range of change, number fluctuations above 140 mg/dL, number fluctuations above 200 mg/dL, percent readings below 80 mg/dL, percent readings above 130 mg/dL, standard error glucose mean, number glucose excursions above standard deviation, mean amplitude of glycemic excursions, J index, interquartile range, mean of daily differences at 6 am, distance traveled, coefficient of variation. The ranges of these values for individuals in the panel are shown in the Table of FIG. 7. Diagnosis was determined based on the American Diabetes Association cutoffs for HbA1c, oral glucose tolerance test at two hours, and fasting blood sugar. Categorization of participants was based on the glycemic signature class in which they spent the largest portion of time.

Effect of Diet Meal Plans on Various Glycemic Regulatory Patterns

To better assess glucose variability among individuals thirty of the participants were next subjected to three standardized meal plans. Each meal plan contained similar calories, but varied in their amounts of proteins, fat and fiber. The meal plans consisted of a breakfast which is when participants had a stable baseline. The breakfast meals were cornflakes and milk (low fiber and high sugar), a peanut butter sandwich (higher fat and higher protein), and a PROBAR protein bar (moderate fat and protein) (See FIG. 15). Each participant consumed the meal twice and for each participant, good reproducibility was observed between replicates (0.5 and 0.4 average Pearson's correlation coefficients between replicates and between individuals, respectively, p-value=1e-08, Wilcoxon test).

The clustering into glucotypes was applied only to a subset of the CGM profiles for each participant, therefore for several participants not all standardized meals were covered by the selected portion of the CGM profile. Thus, a trained clustering was used to classify, or "predict", the entire profiles. To avoid analyzing some responses based on the initial classifications, and others predicted after training, the classes were recomputed for the entire profiles and used those to assign the standardized meal responses to the three glycemic signatures L, M, S. Consistently with the choice of optimal parameters, sliding windows of 2.5 hours with a 75% overlap were used.

To classify the response the standardized meals the windows that were considered started in a 40 minute interval around the annotated consumption time of the meal, i.e. within 20 minutes before or 20 minutes after the meal. The responses were assigned to glucotypes based on the most severe glycemic signature of the overlapping windows.

Figure 16:
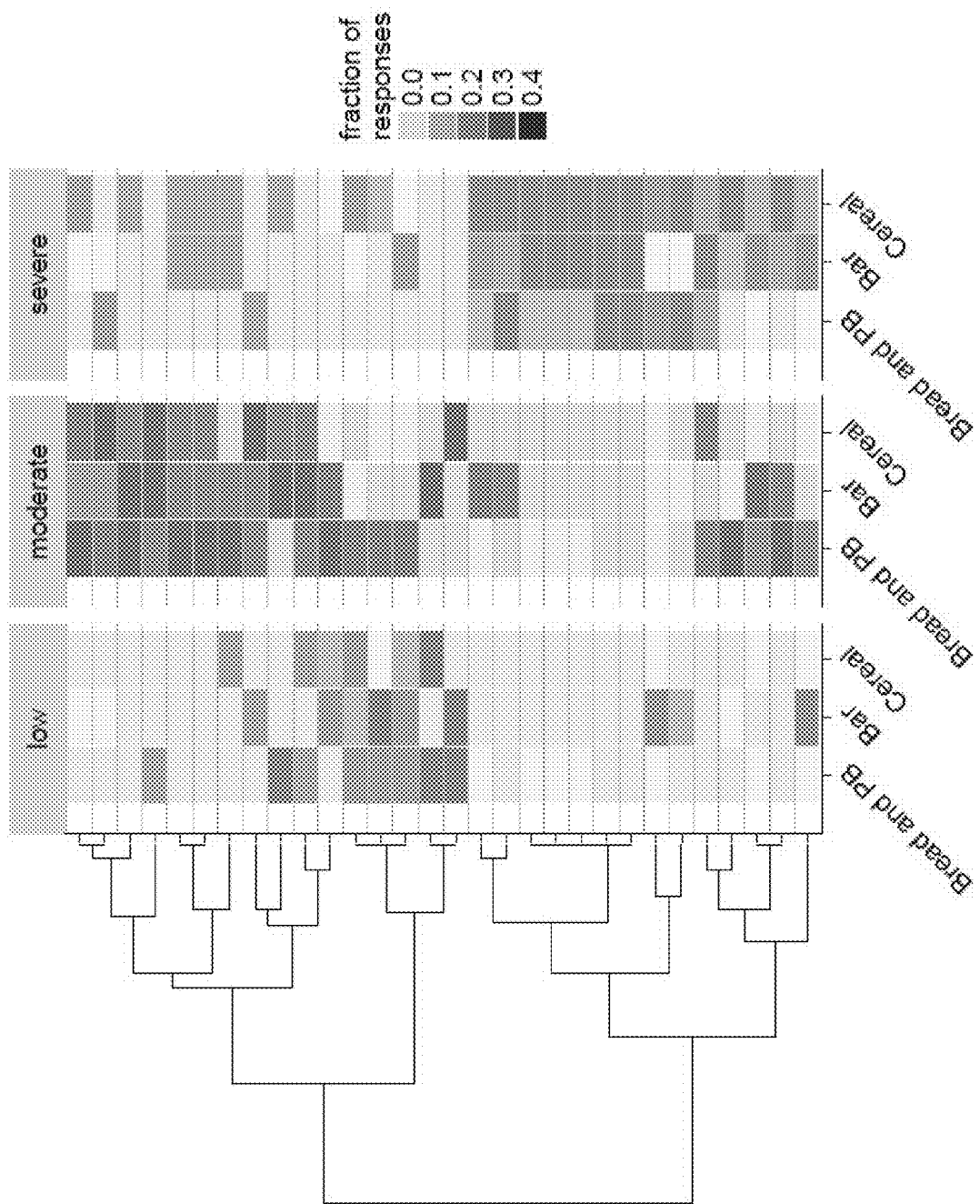
FIG. 16 provides results of responses of three glycemic pattern classes to three different standardized meals, generated in accordance with an embodiment of the invention.
Figure 17:
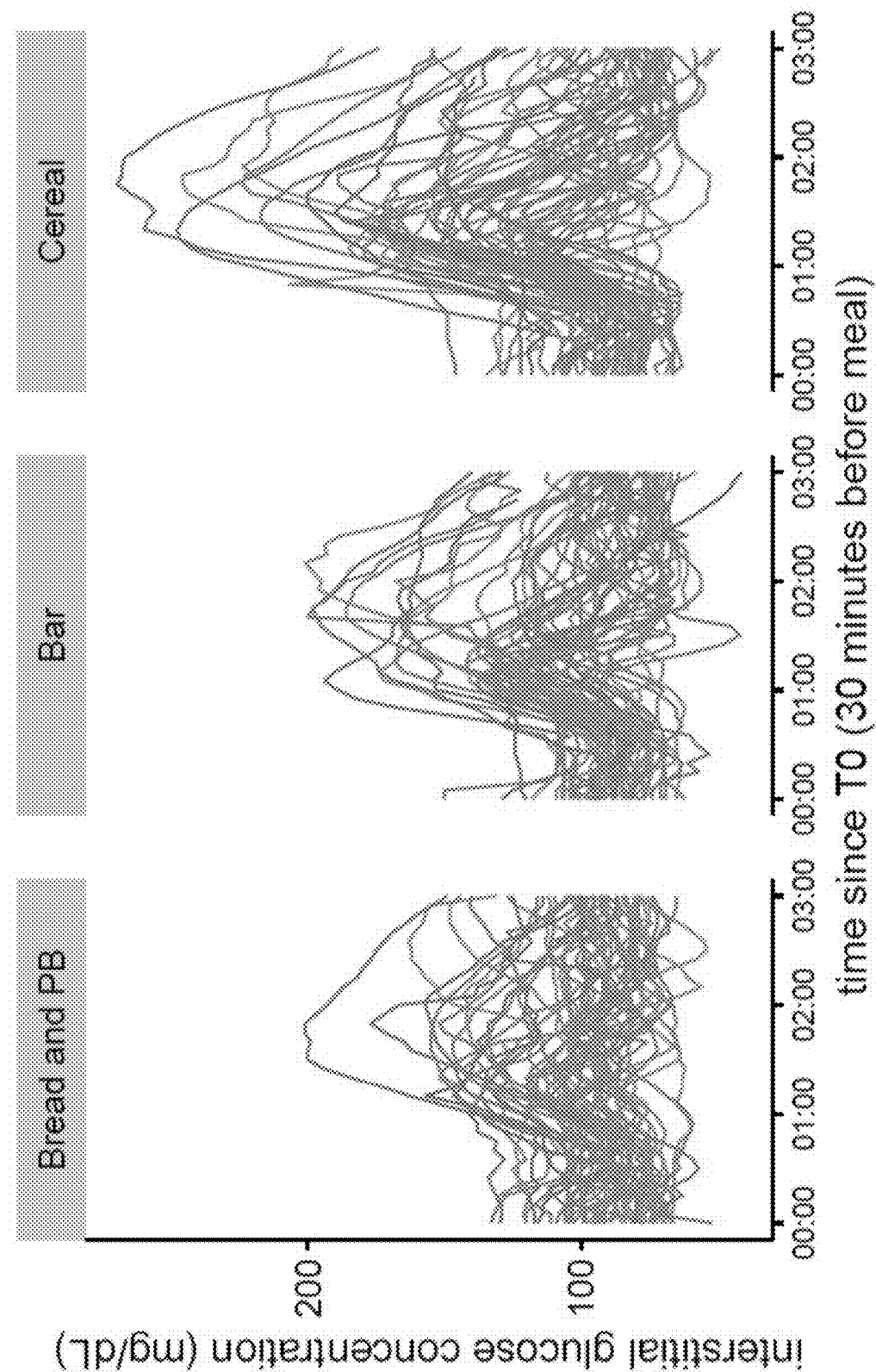
FIG. 17 provides results of interstitial glucose concentration of a number participants in response to standardized meal, generated in accordance with an embodiment of the invention.

Several types of meal responses were found in the panel (FIGS. 16 and 17). Over a majority (60%) of the responses to milk/cereal were classified as severe variability whereas the responses to the PROBAR protein bar and to bread and peanut butter exhibited more low and moderate variability among individuals. Importantly, sixteen subjects who were classified as "normal" based on current standard clinical tests for diagnosing diabetes, had glucose levels in the pre-diabetic (>140 mg/dL) or diabetic (>200 mg/dL) range after the consumption of one or more of the standardized meals (FIG. 16). Additionally, twenty-five subjects had higher glycemic responses measured by CGM following mixed meals than the responses noted on the OGTT, even with similar carbohydrate loading.

To determine the effect of nutrition on these responses, the number of low, moderate and severe responses were correlated with the nutritional content of the meals (FIG. 17). As expected, lower fiber content in cornflakes and milk is associated to more severe responses (FIG. 17, p-value=0.05, chi-squared test). On the other hand, bread and peanut butter, which has more fiber, more fat and more protein, elicits more low or moderate responses (FIG. 17).

Relationship Between Glycemic Regulatory Patterns and Diabetes

Figure 18:
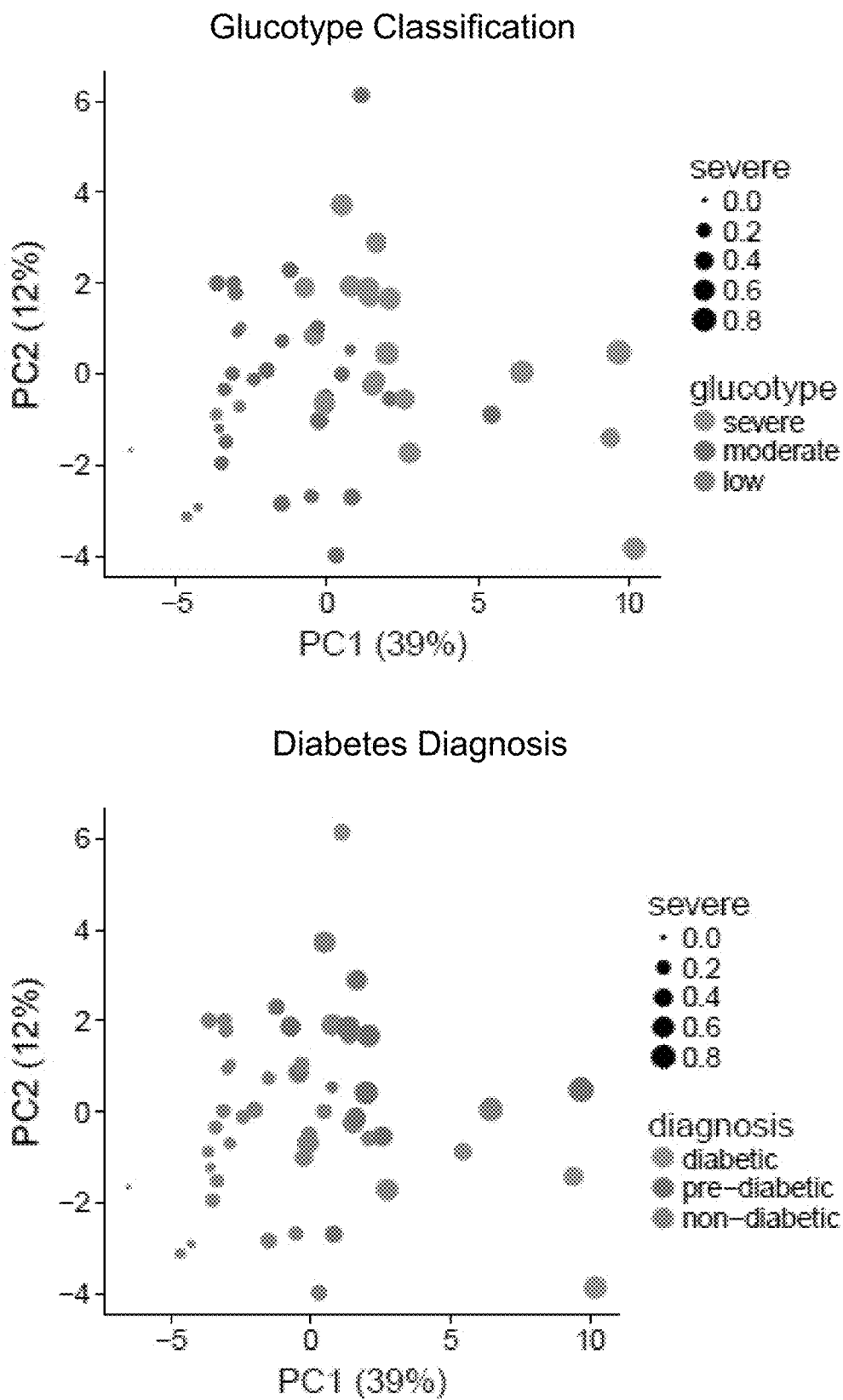
FIG. 18 provides results of principal component analysis of common measures comparing glucotype classification and diabetes diagnosis, generated in accordance with an embodiment of the invention.
Figure 19:
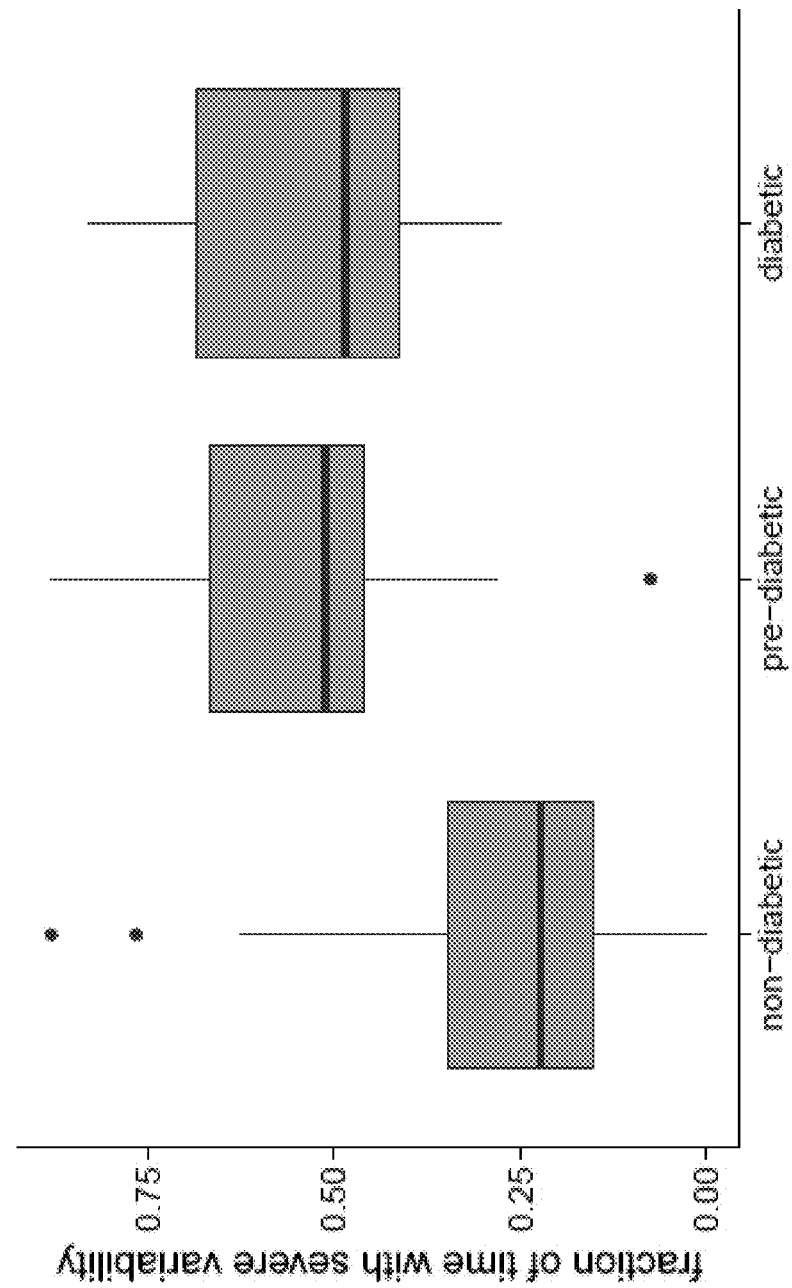
FIG. 19 provides results of the fraction of time spent with severe variability for non-diabetic, pre-diabetic, and diabetic individuals, generated in accordance with an embodiment of the invention.
Figure 20:
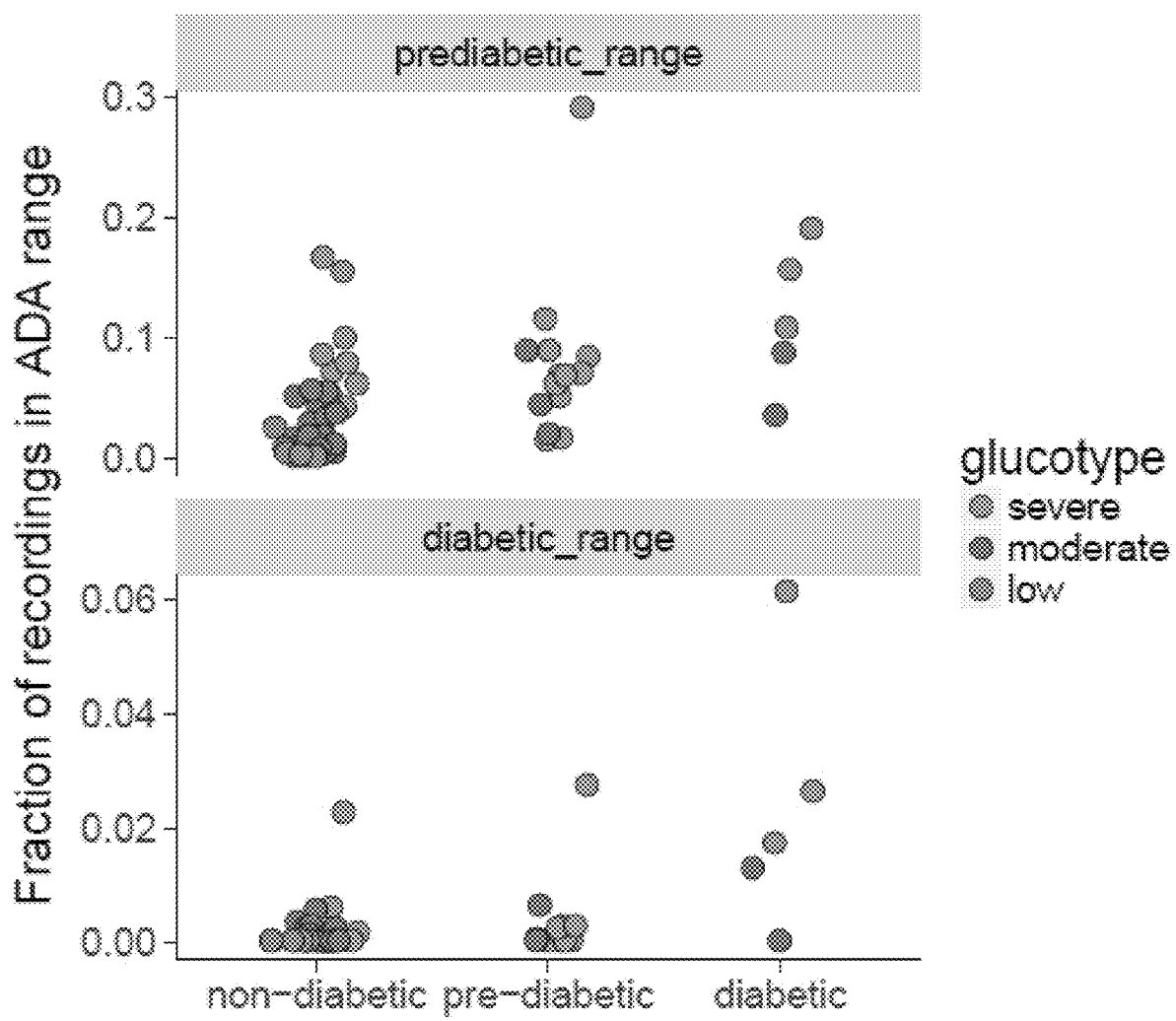
FIG. 20 provides results of proportions of CGM data in pre-diabetic and diabetic glycemic ranges as defined in the American Diabetes Association Guidelines, generated in accordance with an embodiment of the invention.

In order to determine the clinical relevance of the glucotypes, the frequency of these classes in comparison with diabetes diagnosis was examined using OGTT results. A principal component analysis was then used to separate participants by their ability to maintain glucose homeostasis as assessed by clinical glucose metabolic phenotypes and continuous glucose monitoring metrics, such as mean amplitude of glycemic response. The first two components explained slightly over half of the variation in blood sugar control (51%) and are shown in FIG. 18. Glucose control decreases along both principal component one and principal component two, such that the non-diabetic participants are located in the lower-left corner. Many of those with prediabetes were already dominated by severely variable glycemic signatures, which would be expected of diabetic individuals (FIGS. 18 and 19). Furthermore, it was observed that even participants clinically undiagnosed with diabetes or prediabetes can have glucose spikes in pre-diabetic or diabetic range according to the ADA thresholds (FIG. 20). Indeed, normoglycemic patients classified as severe glucotype can reach pre-diabetic glucose levels up to 15% of the duration of CGM recordings, and one non-diabetic patient even surpassed diabetic glucose levels during at least 2% of the recordings (FIG. 20). Thus, normoglycemic individuals can exhibit severe glucotypes with postprandial response similar or exceeding those of diabetics.

Insulin Metabolism of Various Glycemic Regulatory Patterns

There are a number of possible physiological reasons for increased glucose variability, including, but not limited to, insulin resistance and impaired insulin secretion. To further examine the factors underlying variable glucose patterns described by glucotypes, insulin secretion rate, insulin resistance and insulin concentrations we compared between various glucotype patterns (FIG. 21).

Figure 21:
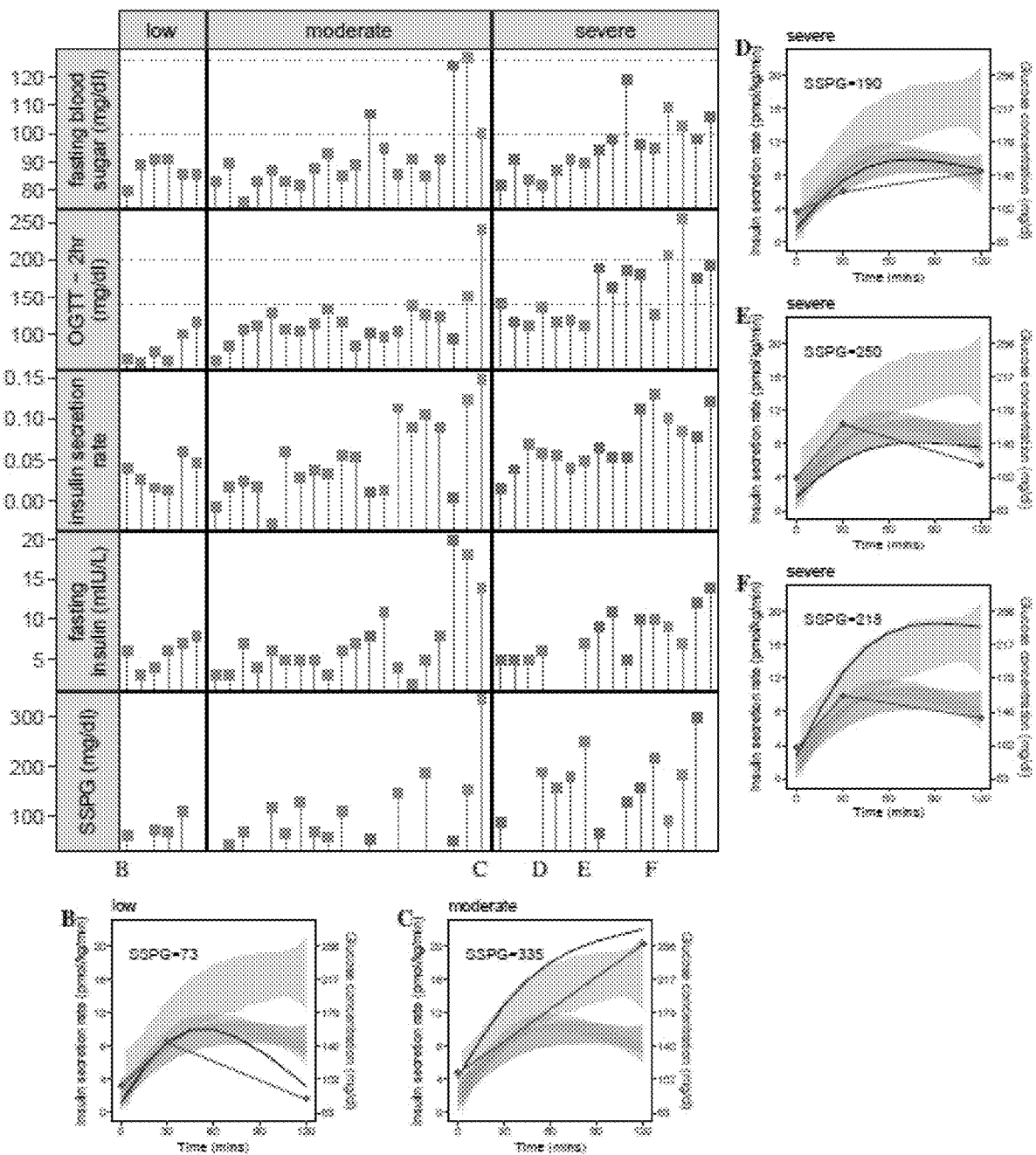
FIG. 21 provides a comparison of glycemic response, insulin secretion, and insulin sensitivity across a spectrum of glucotypes, generated in accordance with an embodiment of the invention.

To demonstrate heterogeneity in insulin metabolism relative to insulin resistance and glucose profiles, dynamic metabolic responses for several individuals are shown in FIG. 21. In general, patients diagnosed with diabetes showed sustained insulin secretion in response to the oral glucose load, although their insulin sensitivity and glycemic responses varied. As an example of normoglycemic participants with low glucose variability, inset B of FIG. 21 shows an insulin sensitive individual with high insulin secretion and a low blood glucose 2 hrs. postprandially. In contrast, inset C of FIG. 21 represents an individual diagnosed with diabetes demonstrating high glycemic concentrations despite high insulin secretion. Presumably this individual is deficient in glucose uptake (i.e. insulin resistant). Insulin metabolism and glucose response was also in 3 undiagnosed individuals according to standard clinical parameters (FIG. 21, insets D, E and F). These include: a nondiabetic individual with normal fasting blood glucose, but high 2 hr. OGTT value in setting of insulin resistance and relative deficiency of insulin secretion (inset D of FIG. 21); a nondiabetic individual with insulin resistance and low insulin secretion, characterized by early glucose rise after load (inset E of FIG. 21); a nondiabetic individual with insulin resistance and high compensatory insulin secretion with relatively normal postprandial glucose following oral glucose load (inset F of FIG. 21).

DOCTRINE OF EQUIVALENTS

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

What is claimed is:

1. A method to treat an individual, comprising:
   fragmenting a first individual's continuous glucose monitoring data into temporally defined windows;
   entering the first individual's temporally defined windows into a dissimilarity matrix that has been constructed using a panel of individuals' temporally defined windows of fragmented continuous glucose monitoring data;
   classifying the first individual's glycemic pattern into a particular class by performing spectral clustering on the dissimilarity matrix,
      wherein the spectral clustering utilizes continuous glucose monitoring data from a panel of individuals to generate a set of classes, and
      wherein the spectral clustering clusters the first individual and each individual of the panel into particular class of the set of classes as determined by each individual's variability in blood glucose levels; and
   treating the first individual based on the individual's glycemic pattern classification.

2. The method according to claim 1, wherein treating the individual is a treatment selected from the group consisting of: medication, dietary supplement, dietary alteration, and physical exercise.

3. The method according to claim 1, wherein the spectral clustering classifies the first individual into a class that is characterized as having greater than moderate glycemic variability, and
   wherein the first individual is administered a medication used to treat type II Diabetes.

4. The method according to claim 3, wherein the medication is selected from the group consisting of: insulin, alpha-glucosidase inhibitors, biguanides, dopamine agonists, DPP-4 inhibitors, glucagon-like peptides, meglitinides, sodium glucose transporter 2 inhibitors, sulfonylureas, and thiazolidinediones.

5. The method according to claim 1, wherein the spectral clustering classifies the first individual into a class that is characterized as having moderate or greater than moderate glycemic variability, and wherein the first individual is administered a dietary supplement selected from the group consisting of: alpha-lipoic acid, chromium, coenzyme Q10, garlic, hydroxychalcone (cinnamon), magnesium, omega-3 fatty acids, psyllium and vitamin D.

6. The method according to claim 1, wherein the temporally defined window has length of: 0.5, 1.0, 1.5, 2.0, 2.5, 3.0, 3.5, 4.0, 4.5, or 5.0 hours.

7. The method according to claim 1, wherein the temporally defined windows overlap to yield a coverage greater than 1×.

8. The method according to claim 1, wherein the fragmentation of continuous glucose monitoring data is determined based upon a parameter selected from the group consisting of: cluster number, proportion of variance explained, average silhouette width, Calinski-Harabasz index, entropy, and Dunn index.

9. The method according to claim 1, wherein the dissimilarity matrix is calculated between all pairs of windows across the first individual.

10. The method according to claim 1, wherein the dissimilarity matrix is calculated using at least one of: complexity invariant distance (CID), dynamic time warping (DTW), Euclidean, and a combination of complexity invariant distance with dynamic time warping (CID-DTW).

11. The method according to claim 1, wherein the spectral clustering is performed using the Luxburg method.

12. The method according to claim 1, wherein the spectral clustering clusters individuals into at least two classes.

13. The method according to claim 12, wherein the spectral clustering clusters individuals into a low glycemic variability class, a moderate glycemic variability class, and a severe glycemic variability class.

14. The method according to claim 12, where the at least two classes are determined without supervision.

15. The method according to claim 1, wherein the first individual has not been diagnosed as diabetic or prediabetic.

16. The method according to claim 15, wherein the first individual has not been diagnosed as normoglycemic.

* * * * *